US007566548B2

(12) United States Patent
Green et al.

(10) Patent No.: US 7,566,548 B2
(45) Date of Patent: Jul. 28, 2009

(54) METHODS FOR IDENTIFYING THERAPEUTIC AGENTS AND FOR TREATING DISEASE

(75) Inventors: Michael Green, Boylston, MA (US); Destin Heilman, Worcester, MA (US); Jose G. Teodoro, Worcester, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 11/204,980

(22) Filed: Aug. 15, 2005

(65) Prior Publication Data

US 2006/0057652 A1    Mar. 16, 2006

Related U.S. Application Data

(60) Provisional application No. 60/601,494, filed on Aug. 13, 2004.

(51) Int. Cl.
*G01N 33/53* (2006.01)
(52) U.S. Cl. .................. 435/7.71; 435/7.91
(58) Field of Classification Search ................ None
See application file for complete search history.

(56) References Cited

U.S. PATENT DOCUMENTS

| 5,491,073 | A | | 2/1996 | Noteborn et al. |
| 5,981,502 | A | * | 11/1999 | Noteborn et al. ............ 514/44 |
| 2005/0014206 | A1 | * | 1/2005 | Vodermaier et al. ........ 435/7.21 |

OTHER PUBLICATIONS

Beroud and Soussi, "The UMD-p53 database: new mutations and analysis tools," *Hum. Mutat.*, 21:176-181 (2003).
Danen-Van Oorschot et al., "Apoptin induces apoptosis in human transformed and malignant cells but not in normal cells," *Proc. Natl. Acad. Sci.*, 94:5843-5847 (1997).
Danen-Van Oorschot et al., "BCL-2 stimulates Apoptin-induced apoptosis," *Adv. Exp. Med. Biol.*, 457:245-249 (1999).
Danen-Van Oorschot et al., "The chicken anemia virus-derived protein apoptin requires activation of caspases for induction of apoptosis in human tumor cells," *J. Virol.*, 74:7072-7078 (2000).
Danen-Van Oorschot et al., "Importance of nuclear localization of apoptin for tumor-specific induction of apoptosis," *J. Biol. Chem.*, 278:27729-27736 (2003).
Genbank Accession No. NM_022662.
Genbank Accession No. NC_001427.
Genbank Accession No. NP_056774 http://www.ncbi.nlm.nih.gov/entrez/query.fcgi?cmd=Retrieve&db=protein&listuids=9626, (retrieved from the internet on Jan. 7, 2003).
Gorlich et al., "Identification of different roles for RanGDP and RanGTP in nuclear protein import," *EMBO J.*, 15:5584-5594 (1996).
Heilman et al., "Apoptin nucleocytoplasmic shuttling is required for cell type-specific localization, apoptosis, and recruitment of the anaphase-promoting complex/cyclosome to PML bodies," *J. Virol.*, 80:7535-45 (2006).

Heilman et al., "The anaphase promoting complex: a critical target for viral proteins and anti-cancer drugs," *Cell Cycle*, 4:560-563 (2005).
Hussain and Harris, "Molecular epidemiology of human cancer: contribution of mutation spectra studies of tumor suppressor genes," *Cancer Res.*, 58:4023-4037 (1998).
Kalland et al., "The human immunodeficiency virus type 1 Rev protein shuttles between the cytoplasm and nuclear compartments," *Mol. Cell. Biol.*, 14:7436-7444 (1994).
Kirn et al., "Replication-selective virotherapy for cancer: Biological principles, risk management and future directions," *Nat. Med.*, 7:781-787 (2001).
Klebe et al., "Interaction of the nuclear GTP-binding protein Ran with its regulatory proteins RCC1 and RanGAP1," *Biochemistry*, 34:639-647 (1995).
Kornitzer et al., "Adenovirus E4orf4 protein induces PP2A-dependent growth arrest in *Saccharomyces cerevisiae* and interacts with the anaphase-promoting complex/cyclosome," *J. Cell Biol.*, 154:331-344 (2001).
Kraft et al., "Mitotic regulation of the human anaphase-promoting complex by phosphorylation," *EMBO J.*, 22:6598-6609 (2003).
Kudo et al., "Leptomycin B inhibition of signal-mediated nuclear export by direct binding to CRM1," *Exp. Cell Res.*, 242:540-547 (1998).
Leliveld et al., "Apoptin induces tumor-specific apoptosis as a globular multimer," *J. Biol. Chem.*, 278:9042-9051 (2003).
Marcellus et al, "The early region 4 orf4 protein of human adenovirus type 5 induces p53-independent cell death by apoptosis," *J. Virol.*, 72: 7144-7153 (1998).
Meyer and Malim, "The HIV-1 Rev trans-activator shuttles between the nucleus and the cytoplasm," *Genes Dev.*, 8:1538-1547 (1994).
Peters et al., "The anaphase-promoting complex: proteolysis in mitosis and beyond," *Mol. Cell.*, 9:931-943 (2002).
Pietersen and Noteborn, "Apoptin," *Adv. Exp. Med. Biol.*, 465:153-161 (2000).
Roulston et al., "Viruses and apoptosis," *Annu. Rev. Microbiol.*, 53:577-628 (1999).
Saffery et al., "Components of the human spindle checkpoint control mechanism localize specifically to the active centromere on dicentric chromosomes," *Hum. Genet.*, 107:376-384 (2000).
Teodoro and Branton, "Regulation of apoptosis by viral gene products," *J. Virol.*, 71:1739-1746 (1997).
Teodoro et al., "The viral protein Apoptin associates with the anaphase-promoting complex to induce G2/M arrest and apoptosis in the absence of p53," *Genes Dev.*, 18:1952-1957 (2004).

(Continued)

*Primary Examiner*—Misook Yu
*Assistant Examiner*—Mark Halvorson
(74) *Attorney, Agent, or Firm*—Fish & Richardson P.C.

(57) ABSTRACT

Included are methods of identifying compounds that mimic the interaction of Apoptin and APC1, e.g., binding of Apoptin to APC1, e.g., dissociation of APC1 from the APC/C, and compounds identified by the methods. Compounds that specifically mimic an interaction of Apoptin and APC1, e.g., cause dissociation of APC1 from the APC/C, are useful for promoting apoptosis (e.g., in cancer cells). Also included are methods of treating a subject having a disorder characterized by aberrant (e.g., decreased) apoptotic processes, by administering a compound that appropriately mimics an interaction of Apoptin and APC1.

16 Claims, 13 Drawing Sheets

OTHER PUBLICATIONS van der Eb et al., Cancer Gene Ther., 9:53-61 (2002).

Venkatesh and Chinnadurai, "Mutants in a conserved region near the carboxy-terminus of HIV-1 Rev identify functionally important residues and exhibit a dominant negative phenotype," *Virology*, 178:327-330 (1990).

Vodermaier et al., "TPR subunits of the anaphase-promoting complex mediate binding to the activator protein CDH1," *Curr. Biol.*, 13:1459-1468 (2003).

Wadia et al., "Apoptin/VP3 contains a concentration-dependent nuclear localization signal (NLS), not a tumorigenic selective NLS," *J. Virol.*, 78, 6077-6078 (2004).

Wirth et al., "Loss of the anaphase-promoting complex in quiescent cells causes unscheduled hepatocyte proliferation," *Genes & Dev.*, 18:88-98 (2004).

Wolff et al., "Leptomycin B is an inhibitor of nuclear export: inhibition of nucleo-cytoplasmic translocation of the human immunodeficiency virus type 1 (HIV-1) Rev protein and Rev-dependent mRNA," *Chem. Biol.*, 4:139-147 (1997).

Zachariae and Nasmyth, "Whose end is destruction: cell division and the anaphase-promoting complex," *Genes Dev.*, 13:2039-2058 (1999).

Zhuang et al., "Apoptin, a protein derived from chicken anemia virus, induces p53-independent apoptosis in human osteosarcoma cells," *Cancer Res.*, 55:486-489 (1995).

\* cited by examiner

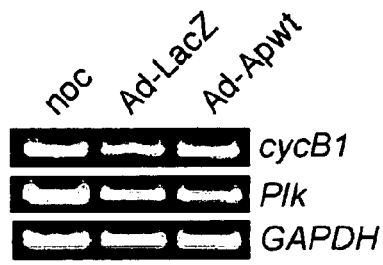

Figure 6

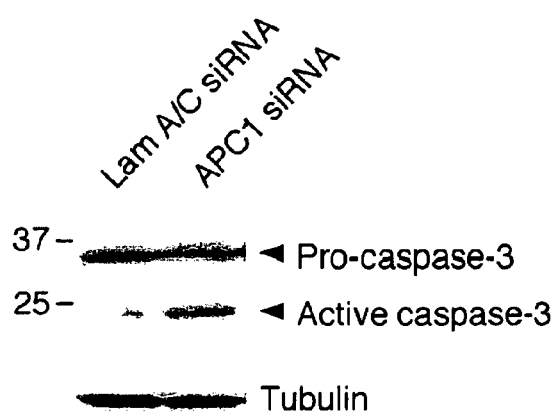

Figure 7

```
  1  atgaacgctc tccaagaaga tactccaccc ggaccatcaa cggtgttcag gccaccaaca
 61  agttcacggc cgttggaaac ccctcactgc agagagatcc ggattggtat cgctggaatt
121  acaatcactc tatcgctgtg tggctgcgcg aatgctcgcg ctcccacgct aagatctgca
181  actgcggaca attcagaaag cactggtttc aagaatgtgc cggacttgag gaccgatcaa
241  cccaagcctc cctcgaagaa gcgatcctgc gaccccctccg agtacagggt aagcgagcta
301  aaagaaagct tgattaccac tactcccagc cgaccccgaa ccgcaaaaag gcgtataaga
361  ctgtaa  (SEQ ID NO:2)
```

Figure 8

```
   1    atgtcgaact tctatgaaga aaggacaacg atgattgcag caagggattt gcaggaattt
  61    gttccttttg gtcgagacca ctgcaagcac cacctaatg ctttgaacct tcaacttcgc
 121    cagctgcagc cagcttctga attatggtct tctgatggtg ctgctggctt ggtgggatcc
 181    cttcaggagg ttacaatcca cgagaaacag aaggaaagct ggcagttaag gaaaggagta
 241    agtgaaattg gagaagatgt ggactatgat gaggaactct atgttgctgg aaatatggtg
 301    atatggagca aaggaagtaa aagccaggca ttggcagttt ataaagcatt tacagttgac
 361    agtcctgttc agcaggcatt gtggtgtgac ttcattatat cacaggataa gtctgaaaag
 421    gcctacagta gcaatgaagt agaaaaatgc atatgtatat tgcaaagctc atgtattaac
 481    atgcatagca tagaaggaaa ggattacata gcttcattac catttcaggt tgcaaatgtt
 541    tggcccacta aatatggatt gctgtttgaa cgaagcgctt cttcacatga agtacctcca
 601    ggttcaccca gagaaccttt acctactatg ttcagcatgc tgcacccact agatgaaata
 661    actccacttg tttgtaaatc tggaagtctt tttggttcat cacgggtgca atatgttgta
 721    gatcatgcaa tgaaaattgt tttcctcaat actgacccct ctattgtaat gacttatgat
 781    gctgttcaaa atgtgcattc tgtgtggact ctccggagag tcaaatcaga ggaagagaat
 841    gttgttttaa agttctctga acaggggga accccacaga atgtggccac tagcagctcc
 901    ctcacagcac atctcagaag cctctccaaa ggagattccc ctgtgacttc acctttccag
 961    aattactcct ccattcacag ccagagtcgc tcaacctcat cacccagtct acattctcgc
1021    tcaccttcta tttccaacat ggcagctcta agtcgtgctc attctcctgc gttaggagtg
1081    cactcttttt caggggtgca aaggttcaac atttcaagcc ataatcagtc tccaaagaga
1141    catagtattt ctcattctcc aaatagtaat tctaatggct cctttcttgc accagaaacg
1201    gagccaattg ttcctgaact gtgtattgac catttgtgga cagaaacgat tactaatata
1261    agagagaaaa attcacaagc ctcaaaagtg tttattacat ctgacctatg tgggcaaaag
1321    ttcctgtgct ttttagtaga gtcccagctc cagttacgct gtgtaaagtt tcaagagagt
1381    aatgataaaa cccagctcat ctttggttca gtgaccaaca taccagcaaa ggatgcagca
1441    ccagtggaga aaatagacac catgctggtc ttggaaggca gtggaaacct ggtgctatac
1501    acaggagtgg ttcgggtggg aaaggttttt attcctggac tgccagctcc ctctctgacg
1561    atgtccaaca caatgcctcg gcccagtact ccactagatg gcgttagtac tccaaagcct
1621    cttagtaaac tccttggatc attggacgag gttgttctgt tgtccccagt tccagaactg
1681    agggattctt caaaacttca tgattctctc tataatgagg attgtacttt ccaacagctt
1741    ggaacttaca ttcattctat cagagatcct gtccataaca gagtcaccct ggaactgagt
1801    aatggctcca tggttaggat cactattcct gaaattgcca cctctgagtt agtacaaacg
1861    tgtttgcaag caattaagtt tatcctgcca aaagaaatag cagttcagat gcttgtcaag
1921    tggtacaatg tccacagtgc tccaggagga cccagttatc actcagagtg gaatttattt
1981    gtgacttgtc tcatgaacat gatgggttat aacacagacc gcttagcatg gactagaaat
2041    tttgactttg aaggatcact ttctcctgtc attgcgccca aaaagcaag gccttcgag
2101    actggatctg atgatgactg gaatattta ctaaattcag actaccacca gaatgttgag
2161    tctcatcttt tgaacagatc tttatgtctg agtccttcag aagcttcaca gatgaaggat
2221    gaggattttt cacagaatct cagtctggat tcttctacac ttctctttac tcacatacct
2281    gcaattttt tcgttcttca ccttgtgtat gaggagctta gttgaatac tctaatggga
2341    gaaggaattt gttcacttgt tgaacttctc gttcagttgg caagggactt aaaattgggg
2401    ccttatgtag atcattacta tagagactac ccaacgcttg tcagaactac tggacaagtg
2461    tgcacaattg atccaggtca aacaggattt atgcatcatc catcattttt tacgtcgag
2521    ccaccaagta tttatcagtg ggtgagttct tgtctgaagg gtgaaggaat gccaccttat
2581    ccttacctcc ctggaatctg tgaaagaagc agacttgtag tcttgagtat tgcactgtac
2641    atacttggtg atgagagctt ggtttctgat gaatcctcac agtatttaac cagaataact
2701    atagcccccc agaagttgca agtagaacaa gaggaaaaca ggtttagttt caggcattct
2761    acatctgttt ctagtctagc tgaaagattg ttgtctgga tgactaatgt aggattcact
2821    ttaagagatt tggaaactct tccctttgga attgctcttc ccatcagaga tgcaatttat
2881    cactgtcgtg agcagcctgc ctcagactgg ccagaagctg tctgtctctt gattggacgt
2941    caggatcttt ccaagcaggc ctgcgaagga aacttcccca agggaagtc tgtgctctca
3001    tcagatgttc cttcaggaac agaaactgag gaggaagatg acggcatgaa tgacatgaat
3061    cacgaggtca tgtcattaat atggagtgaa gatttaaggg tgcaggatgt gcgaaggctt
```

Figure 9A

```
3121 cttcagagtg cgcatcctgt ccgtgtcaac gtagtgcagt acccagagct cagtgaccac
3181 gagttcatcg aggaaaagga aaacagattg ctccaattgt gtcagcgaac tatggctctt
3241 cctgtaggac gaggaatgtt taccttgttt tcgtaccatc ctgttccaac agagccattg
3301 cctattccta aattgaatct gactgggcgt gccctcctc ggaacacaac agtagacctt
3361 aatagtggaa acatcgatgt gcctcccaac atgacaagct gggccagctt tcataatggt
3421 gtggctgctg cctgaagat agctcctgcc tcccagatcg actcagcttg gattgtttac
3481 aataagccca agcatgctga gttggccaat gagtatgctg gctttctcat ggctctgggt
3541 ttgaatgggc accttaccaa gctggcgact ctcaatatcc atgactactt gaccaagggc
3601 catgaaatga caagcattgg actgctactt ggtgtttctg ctgcaaaact aggcaccatg
3661 gatatgtcta ttactcggct tcttagcatt cacattcctg ctctcttacc cccaacgtcc
3721 acagagctgg atgttcctca caatgtccaa gtggctgcag tggttggcat tggccttgta
3781 tatcaaggga cagctcacag acatactgca gaagtcctgt tggctgagat aggacggcct
3841 cctggtcctg aaatggaata ctgcactgac agagagtcat actccttagc tgctggcttg
3901 gccctgggca tggtctgctt ggggcatggc agcaatttga taggtatgtc tgatctcaat
3961 gtgcctgagc agctctatca gtacatggtt ggaggacata ggcgctttca aacaggaatg
4021 cataggagaa aacataaatc accaagttat caaatcaaag aaggagatac cataaatgtg
4081 gatgtgactt gtccaggtgc tactctagct ttggctatga tctacttaaa aaccaataac
4141 agatctattg cagattggct ccgagcccct gacaccatgt atttgttgga ctttgtgaag
4201 ccagaatttc tcttgcttag gacacttgct cgatgcctga ttttgtggga tgatatttta
4261 ccaaattcca agtgggttga cagcaatgtt cctcaaatta aagagaaaa tagtatctct
4321 ctcagtgaaa tcgaattgcc gtgctcagag gatttgaatt tggaaacttt gtcccaagca
4381 catgtctaca taattgcagg agcctgcttg tctctgggtt ttcgatttgc tggctcagaa
4441 aacttatcag catttaactg tttgcataaa tttgccaaag attttatgac ttatttgtcc
4501 gcacctaatg cttctgttac aggtcctcat aacctagaaa cttgtctgag cgtggtgctg
4561 ctgtctctcg ccatggtcat ggctggctca ggaaacctaa aggttttgca gctttgtcgc
4621 ttcttacaca tgaaaacggg tggtgaaatg aactatggtt tcacttagc ccaccacatg
4681 gcccttggac ttctattttt gggaggagga aggtactctt tgagcacatc aaattcttcc
4741 attgccgctc ttctctgtgc cctttatccg cacttcccag ctcacagcac tgacaaccgg
4801 tatcatctcc aggctctccg gcacctctat gtgctggccg cggagcccag gcttctagtg
4861 cctgtggatg tggacacaaa cacgccctgc tatgccctct tagaagttac ctacaagggc
4921 actcagtggt atgaacaaac caaagaagaa ttgatggctc ctacccttct tccagaactc
4981 catctttttaa agcagattaa agtaaaaggc caagatact gggaactgct catagattta
5041 agcaaaggaa cacaacactt gaagtccatc cttccaagg atggggtttt atatgttaaa
5101 ctccgggcgg gtcagctctc ctacaaagaa gatccaatgg gatggcaaag tttgttggct
5161 cagactgttg ctaacaggaa ctctgaagcc cgggctttca agccagaaac aatctcagca
5221 ttcacttctg atccagcact tctgtcattt gctgaatatt tctgcaagcc aactgtgaac
5281 atgggtcaga aacaggaaat tctggatctc ttttcttcag tactctatga atgtgttacc
5341 caggagaccc cagagatgtt gcctgcatac atagcaatgg atcaggctat aagaagactt
5401 gggagaagag aaatgtctga gacttctgaa ctttggcaga taaagttggt gttagagttt
5461 ttcagctccc gaagccatca ggagcggctg cagaaccacc ctaagcgggg gctctttatg
5521 aactcggaat tcctccctgt tgtgaagtgc accattgata taccctgga ccagtggcta
5581 caagtcgggg gtgatatgtg tgtgcacgcc tacctcagcg ggcagccctt ggaggaatca
5641 cagctgagca tgctggcctg cttcctcgtc taccactctg tgccagctcc acagcacctg
5701 ccacctatag gactagaagg gagcacaagc tttgctgaac tgctcttcaa atttaagcag
5761 ctaaaaatgc cagtgcgagc tttgctgaga ttggctcctt tgcttcttgg aaatccacag
5821 ccaatggtga tgtga   (SEQ ID NO:15)
```

Figure 9B

SEQUENCE LISTING

<160> NUMBER OF SEQ ID NOS: 19

<210> SEQ ID NO 1
<211> LENGTH: 121
<212> TYPE: PRT
<213> ORGANISM: Chicken anemia virus

<400> SEQUENCE: 1

Met Asn Ala Leu Gln Glu Asp Thr Pro Pro Gly Pro Ser Thr Val Phe
1               5                   10                  15

Arg Pro Pro Thr Ser Ser Arg Pro Leu Glu Thr Pro His Cys Arg Glu
            20                  25                  30

Ile Arg Ile Gly Ile Ala Gly Ile Thr Ile Thr Leu Ser Leu Cys Gly
        35                  40                  45

Cys Ala Asn Ala Arg Ala Pro Thr Leu Arg Ser Ala Thr Ala Asp Asn
    50                  55                  60

```
Ser Glu Ser Thr Gly Phe Lys Asn Val Pro Asp Leu Arg Thr Asp Gln
 65                  70                  75                  80

Pro Lys Pro Pro Ser Lys Lys Arg Ser Cys Asp Pro Ser Glu Tyr Arg
                 85                  90                  95

Val Ser Glu Leu Lys Glu Ser Leu Ile Thr Thr Thr Pro Ser Arg Pro
            100                 105                 110

Arg Thr Ala Lys Arg Arg Ile Arg Leu
        115                 120

<210> SEQ ID NO 2
<211> LENGTH: 366
<212> TYPE: DNA
<213> ORGANISM: Chicken anemia virus

<400> SEQUENCE: 2
atgaacgctc tccaagaaga tactccaccc ggaccatcaa cggtgttcag gccaccaaca      60
agttcacggc cgttggaaac ccctcactgc agagagatcc ggattggtat cgctggaatt     120
acaatcactc tatcgctgtg tggctgcgcg aatgctcgcg ctcccacgct aagatctgca     180
actgcggaca attcagaaag cactggtttc aagaatgtgc cggacttgag gaccgatcaa     240
cccaagcctc cctcgaagaa gcgatcctgc gaccccgtcg agtacagggt aagcgagcta     300
aaagaaagct tgattaccac tactcccagc cgaccccgaa ccgcaaaaag gcgtataaga     360
ctgtaa                                                                366

<210> SEQ ID NO 3
<211> LENGTH: 46
<212> TYPE: DNA
<213> ORGANISM: Artificial Sequence
<220> FEATURE:
<223> OTHER INFORMATION: Primer

<400> SEQUENCE: 3
gcgtaatacg actcactata gggagaaaag gagtaagtga aattgg                     46

<210> SEQ ID NO 4
<211> LENGTH: 46
<212> TYPE: DNA
<213> ORGANISM: Artificial Sequence
<220> FEATURE:
<223> OTHER INFORMATION: Primer

<400> SEQUENCE: 4
gcgtaatacg actcactata gggagaggaa aggtgaagtc acaggg                     46

<210> SEQ ID NO 5
<211> LENGTH: 46
<212> TYPE: DNA
<213> ORGANISM: Artificial Sequence
<220> FEATURE:
<223> OTHER INFORMATION: Primer

<400> SEQUENCE: 5
gcgtaatacg actcactata gggagaggca gtctgctgag aggaac                     46

<210> SEQ ID NO 6
<211> LENGTH: 46
<212> TYPE: DNA
<213> ORGANISM: Artificial Sequence
<220> FEATURE:
<223> OTHER INFORMATION: Primer

<400> SEQUENCE: 6
```

```
gcgtaatacg actcactata gggagaaggt gttctgtgcc ttccac                         46

<210> SEQ ID NO 7
<211> LENGTH: 1515
<212> TYPE: DNA
<213> ORGANISM: Homo sapiens

<400> SEQUENCE: 7
aaattggggc ttatgtagat tcattactat agagactacc caacgcttgt cagaactact          60
ggacaagtgt gcacaattga tccaggtcaa acaggattta tgcatcatcc atcatttttt         120
acgtctgagc caccaagtat ttatcagtgg gtgagttctt gtctgaaggg tgaaggaatg         180
ccaccttatc cttacctccc tggaatctgt gaaagaagca gacttgtagt cttgagtatt         240
gcactgtaca tacttggtga tgagagcttg gtttctgatg aatcctcaca gtatttaacc         300
agaataacta tagcccccca gaagttgcaa gtagaacaag aggaaaacag gtttagtttc         360
aggcattcta catctgtttc tagtctagct gaaagattgg ttgtctggat gactaatgta         420
ggattcactt taagagattt ggaaactctt ccctttggaa ttgctcttcc catcagagat         480
gcaatttatc actgtcgtga gcagcctgcc tcagactggc cagaagctgt ctgtctcttg         540
attggacgtc aggatctttc caagcaggcc tgcgaaggaa acttacccaa agggaagtct         600
gtgctctcat cagatgttcc ttcaggaaca gaaactgagg aggaagatga cggcatgaat         660
gacatgaatc acgaggtcat gtcattaata tggagtgaag atttaagggt gcaggatgtg         720
cgaaggcttc ttcagagtgc gcatcctgtc cgtgtcaacg tagtgcagta cccagagctc         780
agtgaccacg agttcatcga ggaaaaggaa aacagattgc tccaattgtg tcagcgaact         840
atggctcttc ctgtaggacg aggaatgttt accttgtttt cgtaccatcc tgttccaaca         900
gagccattgc ctattcctaa attgaatctg actgggcgtg cccctcctcg aacacaaca         960 gtagacctta atagtggaaa catcgatgtg cctcccaaca tgacaagctg gccagcttt         1020 cataatggtg tggctgctgg cctgaagata gctcctgcct cccagatcga ctcagcttgg        1080
attgtttaca ataagcccaa gcatgctgag ttggccaatg agtatgctgg ctttctcatg        1140
gctctgggtt tgaatgggca ccttaccaag ctggcgactc tcaatatcca tgactacttg        1200
accaagggcc atgaaatgac aagcattgga ctgctacttg tgtttctgc tgcaaaacta         1260 ggcaccatgg atatgtctat tactcggctt cttagcattc acattcctgc tctcttaccc         1320
ccaacgtcca cagagctgga tgttcctcac aatgtccaag tggctgcagt ggttggcatt        1380
ggccttgtat atcaagggac agctcacaga catactgcag aagtcctgtt ggctgagata        1440
ggacggcctc ctggtcctga aatggaatac tgcactgaca gagagtcata ctccttagct       1500
gctggcttgg ccctg                                                         1515

<210> SEQ ID NO 8
<211> LENGTH: 1067
<212> TYPE: DNA
<213> ORGANISM: Homo sapiens

<400> SEQUENCE: 8
gaggaactgg acttccagaa gaacatctac agtgaggagc tgcgtgagac caagcgccgt          60
catgagaccc gactggtgga gattgacaat gggaagcagc gtgagtttga gagccggctg        120
gcggatgcgc tgcaggaact gcgggcccag catgaggacc aggtggagca gtataagaag        180
gagctggaga agacttattc tgccaagctg gacaatgcca ggcagtctgc tgagaggaac        240
```

```
agcaacctgg tgggggctgc ccacgaggag ctgcagcagt cgcgcatccg catcgacagc    300
ctctctgccc agctcagcca gctccagaag cagctggcag ccaaggaggc gaagcttcga    360
gacctggagg actcactggc ccgtgagcgg acaccagcc ggcggctgct ggcggaaaag     420
gagcgggaga tggccgagat gcgggcaagg atgcagcagc agctggacga gtaccaggag    480
cttctggaca tcaagctggc cctggacatg gagatccacg cctaccgcaa gctcttggag    540
ggcgaggagg agaggctacg cctgtccccc agccctacct cgcagcgcag ccgtggccgt    600
gcttcctctc actcatccca gacacagggt gggggcagcg tcaccaaaaa gcgcaaactg    660
gagtccactg agagccgcag cagcttctca cagcacgcac gcactagcgg gcgcgtggcc    720
gtggaggagg tggatgagga gggcaagttt gtccggctgc gcaacaagtc caatgaggac    780
cagtccatgg gcaattggca gatcaagcgc cagaatggga tgatcccctt gctgacttac    840
cggttcccac caaagttcac cctgaaggct gggcaggtgg tgacgatctg ggctgcagga    900
gctgggccca cccacagccc ccctaccgac ctggtgtgga aggcacagaa cacctggggc    960
tgcgggaaca gcctgcgtac ggctctcatc aactccactg gggaagaagt ggccatgcgc   1020
aagctggtgc gctcagtgac tgtggttgag gacgacgagg atgagga                1067
```

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
tactgcctct ccaagcccaa tg                                              22

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
cgtgaaggaa gcctctcgta ga                                              22

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
attcccaagc acatcaaccc cgtg                                            24

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
gagatgttac taccactgtc ggac                                            24

<210> SEQ ID NO 13
<211> LENGTH: 20

```
<212> TYPE: DNA
<213> ORGANISM: Artificial Sequence
<220> FEATURE:
<223> OTHER INFORMATION: Primer

<400> SEQUENCE: 13
accacagtcc atgccatcac                                                   20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
atgtcgttgt cccaccacct                                                   20

<210> SEQ ID NO 15
<211> LENGTH: 5835
<212> TYPE: DNA
<213> ORGANISM: Homo sapiens

<400> SEQUENCE: 15
atgtcgaact tctatgaaga aaggacaacg atgattgcag caagggattt gcaggaattt       60
gttccttttg gtcgagacca ctgcaagcac caccctaatg ctttgaacct tcaacttcgc      120
cagctgcagc cagcttctga attatggtct tctgatggtg ctgctggctt ggtgggatcc      180
cttcaggagg ttacaatcca cgagaaacag aaggaaagct ggcagttaag gaaaggagta      240
agtgaaattg gagaagatgt ggactatgat gaggaactct atgttgctgg aaatatggtg      300
atatggagca aaggaagtaa aagccaggca ttggcagttt ataaagcatt tacagttgac      360
agtcctgttc agcaggcatt gtggtgtgac ttcattatat cacaggataa gtctgaaaag      420
gcctacagta gcaatgaagt agaaaaatgc atatgtatat tgcaaagctc atgtattaac      480
atgcatagca tagaaggaaa ggattacata gcttcattac catttcaggt tgcaaatgtt      540
tggcccacta aatatggatt gctgtttgaa cgaagcgctt cttcacatga agtacctcca      600
ggttcaccca gagaaccttt acctactatg ttcagcatgc tgcacccact agatgaaata      660
actccacttg tttgtaaatc tggaagtctt tttggttcat cacgggtgca atatgttgta      720
gatcatgcaa tgaaaattgt tttcctcaat actgacccct ctattgtaat gacttatgat      780
gctgttcaaa atgtgcattc tgtgtggact ctccggagag tcaaatcaga ggaagagaat      840
gttgttttaa agttctctga acaggggga accccacaga atgtggccac tagcagctcc      900
ctcacagcac atctcagaag cctctccaaa ggagattccc ctgtgacttc acctttccag      960
aattactcct ccattcacag ccagagtcgc tcaacctcat cacccagtct acattctcgc     1020
tcaccttcta tttccaacat ggcagctcta agtcgtgctc attctcctgc gttaggagtg     1080
cactcttttt caggggtgca aaggttcaac atttcaagcc ataatcagtc tccaaagaga     1140
catagtattt ctcattctcc aaatagtaat tctaatggct cctttcttgc accagaaacg     1200
gagccaattg ttcctgaact gtgtattgac catttgtgga cagaaacgat tactaatata     1260
agagagaaaa attcacaagc ctcaaaagtg tttattacat ctgacctatg tgggcaaaag     1320
ttcctgtgct ttttagtaga gtcccagctc cagttacgct gtgtaaagtt tcaagagagt     1380
aatgataaaa cccagctcat ctttggttca gtgaccaaca taccagcaaa ggatgcagca     1440
ccagtggaga aaatagacac catgctggtc ttggaaggca gtggaaacct ggtgctatac     1500
```

```
acaggagtgg ttcgggtggg aaaggttttt attcctggac tgccagctcc ctctctgacg   1560
atgtccaaca caatgcctcg gcccagtact ccactagatg gcgttagtac tccaaagcct   1620
cttagtaaac tccttggatc attggacgag gttgttctgt tgtccccagt tccagaactg   1680
agggattctt caaaacttca tgattctctc tataatgagg attgtacttt ccaacagctt   1740
ggaacttaca ttcattctat cagagatcct gtccataaca gagtcaccct ggaactgagt   1800
aatggctcca tggttaggat cactattcct gaaattgcca cctctgagtt agtacaaacg   1860
tgtttgcaag caattaagtt tatcctgcca aaagaaatag cagttcagat gcttgtcaag   1920
tggtacaatg tccacagtgc tccaggagga cccagttatc actcagagtg gaatttattt   1980
gtgacttgtc tcatgaacat gatgggttat aacacagacc gcttagcatg gactagaaat   2040
tttgactttg aaggatcact ttctcctgtc attgcgccca aaaaagcaag gccttccgag   2100
actggatctg atgatgactg ggaatattta ctaaattcag actaccacca gaatgttgag   2160
tctcatcttt tgaacagatc tttatgtctg agtccttcag aagcttcaca gatgaaggat   2220
gaggattttt cacagaatct cagtctggat tcttctacac ttctctttac tcacatacct   2280 gcaattttt tcgttcttca ccttgtgtat gaggagctta agttgaatac tctaatggga   2340
gaaggaattt gttcacttgt tgaacttctc gttcagttgg caagggactt aaaattgggg   2400
ccttatgtag atcattacta tagagactac ccaacgcttg tcagaactac tggacaagtg   2460
tgcacaattg atccaggtca aacaggattt atgcatcatc catcattttt tacgtctgag   2520
ccaccaagta tttatcagtg ggtgagttct tgtctgaagg gtgaaggaat gccaccttat   2580
ccttacctcc ctggaatctg tgaaagaagc agacttgtag tcttgagtat tgcactgtac   2640
atacttggtg atgagagctt ggtttctgat gaatcctcac agtatttaac cagaataact   2700
atagcccccc agaagttgca agtagaacaa gaggaaaaca ggtttagttt caggcattct   2760
acatctgttt ctagtctagc tgaaagattg gttgtctgga tgactaatgt aggattcact   2820
ttaagagatt tggaaactct tcccttttgga attgctcttc ccatcagaga tgcaatttat   2880
cactgtcgtg agcagcctgc ctcagactgg ccagaagctg tctgtctctt gattggacgt   2940
caggatcttt ccaagcaggc ctgcgaagga aacttaccca aagggaagtc tgtgctctca   3000
tcagatgttc cttcaggaac agaaactgag gaggaagatg acggcatgaa tgacatgaat   3060
cacgaggtca tgtcattaat atggagtgaa gatttaaggg tgcaggatgt gcgaaggctt   3120
cttcagagtg cgcatcctgt ccgtgtcaac gtagtgcagt acccagagct cagtgaccac   3180
gagttcatcg aggaaaagga aaacagattg ctccaattgt gtcagcgaac tatggctctt   3240
cctgtaggac gaggaatgtt taccttgttt tcgtaccatc ctgttccaac agagccattg   3300
cctattccta aattgaatct gactgggcgt gcccctcctc ggaacacaac agtagacctt   3360
aatagtggaa acatcgatgt gcctcccaac atgacaagct gggccagctt tcataatggt   3420
gtggctgctg gcctgaagat agctcctgcc tcccagatcg actcagcttg gattgtttac   3480
aataagccca gcatgctgat gttggccaat gagtatgctg gctttctcat ggctctgggt   3540
ttgaatgggc accttaccaa gctggcgact ctcaatatcc atgactactt gaccaagggc   3600
catgaaatga caagcattgg actgctactt ggtgtttctg ctgcaaaact aggcaccatg   3660
gatatgtcta ttactcggct tcttagcatt cacattcctg ctctcttacc cccaacgtcc   3720
acagagctgg atgttcctca caatgtccaa gtggctgcag tggttggcat tggccttgta   3780
tatcaaggga cagctcacag acatactgca gaagtcctgt tggctgagat aggacgggcct   3840 cctggtcctg aaatggaata ctgcactgac agagagtcat actccttagc tgctggcttg   3900
```

-continued gccctgggca tggtctgctt ggggcatggc agcaatttga taggtatgtc tgatctcaat 3960
gtgcctgagc agctctatca gtacatggtt ggaggacata ggcgctttca aacaggaatg 4020
catagggaga aacataaatc accaagttat caaatcaaag aaggagatac cataaatgtg 4080
gatgtgactt gtccaggtgc tactctagct ttggctatga tctacttaaa aaccaataac 4140
agatctattg cagattggct ccgagcccct gacaccatgt atttgttgga ctttgtgaag 4200
ccagaatttc tcttgcttag gacacttgct cgatgcctga ttttgtggga tgatatttta 4260
ccaaattcca agtgggttga cagcaatgtt cctcaaatta taagagaaaa tagtatctct 4320
ctcagtgaaa tcgaattgcc gtgctcagag gatttgaatt tggaaacttt gtcccaagca 4380
catgtctaca taattgcagg agcctgcttg tctctgggtt ttcgatttgc tggctcagaa 4440
aacttatcag catttaactg tttgcataaa tttgccaaag attttatgac ttatttgtcc 4500
gcacctaatg cttctgttac aggtcctcat aacctagaaa cttgtctgag cgtggtgctg 4560
ctgtctctcg ccatggtcat ggctggctca ggaaacctaa aggttttgca gctttgtcgc 4620
ttcttacaca tgaaaacggg tggtgaaatg aactatggtt ttcacttagc ccaccacatg 4680
gcccttggac ttctattttt gggaggagga aggtactctt tgagcacatc aaattcttcc 4740
attgccgctc ttctctgtgc cctttatccg cacttcccag ctcacagcac tgacaaccgg 4800
tatcatctcc aggctctccg gcacctctat gtgctggccg cggagcccag gcttctagtg 4860
cctgtggatg tggacacaaa cacgccctgc tatgccctct tagaagttac ctacaagggc 4920
actcagtggt atgaacaaac caaagaagaa ttgatggctc ctacccttct tccagaactc 4980
catcttttaa agcagattaa agtaaaaggc ccaagatact gggaactgct catagattta 5040
agcaaaggaa cacaacactt gaagtccatc ctttccaagg atggggtttt atatgttaaa 5100
ctccgggcgg gtcagctctc ctacaaagaa gatccaatgg gatggcaaag tttgttggct 5160
cagactgttg ctaacaggaa ctctgaagcc cgggctttca agccagaaac aatctcagca 5220
ttcacttctg atccagcact tctgtcattt gctgaatatt tctgcaagcc aactgtgaac 5280
atgggtcaga aacaggaaat tctggatctc ttttcttcag tactctatga atgtgttacc 5340
caggagaccc cagagatgtt gcctgcatac atagcaatgg atcaggctat aagaagactt 5400
gggagaagag aaatgtctga gacttctgaa ctttggcaga taaagttggt gttagagttt 5460
ttcagctccc gaagccatca ggagcggctg cagaaccacc ctaagcgggg gctctttatg 5520
aactcggaat tcctccctgt tgtgaagtgc accattgata ataccctgga ccagtggcta 5580
caagtcgggg gtgatatgtg tgtgcacgcc tacctcagcg ggcagccctt ggaggaatca 5640
cagctgagca tgctggcctg cttcctcgtc taccactctg tgccagctcc acagcacctg 5700
ccacctatag gactagaagg gagcacaagc tttgctgaac tgctcttcaa atttaagcag 5760
ctaaaaatgc cagtgcgagc tttgctgaga ttggctcctt tgcttcttgg aaatccacag 5820
ccaatggtga tgtga 5835

<210> SEQ ID NO 16
<211> LENGTH: 80
<212> TYPE: PRT
<213> ORGANISM: Chicken anemia virus

<400> SEQUENCE: 16

Ile Thr Leu Ser Leu Cys Gly Cys Ala Asn Ala Arg Ala Pro Thr Leu
1 5 10 15

Arg Ser Ala Thr Ala Asp Asn Ser Glu Ser Thr Gly Phe Lys Asn Val

```
                         20                  25                  30
Pro Asp Leu Arg Thr Asp Gln Pro Lys Pro Pro Ser Lys Lys Arg Ser
            35                  40                  45

Cys Asp Pro Ser Glu Tyr Arg Val Ser Glu Leu Lys Glu Ser Leu Ile
 50                  55                  60

Thr Thr Thr Pro Ser Arg Pro Arg Thr Ala Lys Arg Ile Arg Leu
 65                  70                  75                  80

<210> SEQ ID NO 17
<211> LENGTH: 40
<212> TYPE: PRT
<213> ORGANISM: Chicken anemia virus

<400> SEQUENCE: 17

Lys Pro Pro Ser Lys Lys Arg Ser Cys Asp Pro Ser Glu Tyr Arg Val
 1               5                  10                  15

Ser Glu Leu Lys Glu Ser Leu Ile Thr Thr Thr Pro Ser Arg Pro Arg
            20                  25                  30

Thr Ala Lys Arg Ile Arg Leu
            35                  40

<210> SEQ ID NO 18
<211> LENGTH: 7
<212> TYPE: PRT
<213> ORGANISM: Artificial Sequence
<220> FEATURE:
<223> OTHER INFORMATION: Synthetically generated peptide

<400> SEQUENCE: 18

Pro Lys Lys Lys Arg Lys Val
 1               5

<210> SEQ ID NO 19
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 19

Ile Ala Gly Ile Thr Ile Thr Leu Ser Leu
 1               5                  10
```

METHODS FOR IDENTIFYING THERAPEUTIC AGENTS AND FOR TREATING DISEASE

CLAIM OF PRIORITY

This application claims priority under 35 USC §119(e) to U.S. Provisional Patent Application Ser. No. 60/601,494, filed on Aug. 13, 2004, the entire contents of which are hereby incorporated by reference.

FEDERALLY SPONSORED RESEARCH OR DEVELOPMENT

This invention was made with Government support under Grant No. A131272, awarded by the National Institutes of Health. The Government has certain rights in the invention.

TECHNICAL FIELD

This invention relates to methods of screening for therapeutic agents, the agents identified thereby, and their use in treating disease, e.g., cancer or degenerative diseases.

BACKGROUND

Apoptosis is a physiological form of cell death that is required during normal development and plays a key role in controlling disease by mediating the elimination of cancerous or virus-infected cells. Many animal viruses have been found to regulate apoptosis (reviewed in Teodoro and Branton, J. Virol., 71:1739-1746 (1997); Roulston et al., Annu. Rev. Microbiol., 53: 577-628 (1999)). Inhibition of apoptosis can maximize viral replication efficiency and help evade an immune response. Conversely, induction of apoptosis near the end of virus replication can facilitate viral egress.

The development of novel and effective cancer therapies depends in part upon the discovery of agents that selectively destroy tumor cells while leaving normal cells intact. Several viruses have such selective intrinsic oncolytic activity or have been engineered to become oncolytic (reviewed in Kim et al., Nat. Med., 7:781-787 (2001)). For example, the Chicken Anemia Virus protein Apoptin can induce apoptosis in a variety of human malignant cell lines (Zhuang et al., Cancer Res., 55:486-489 (1995)). Two properties of Apoptin-induced cell death are important to note. First, Apoptin does not induce apoptosis in normal (untransformed) cells (reviewed in Pietersen and Noteborn, Adv. Exp. Med. Biol., 465:153-161 (2000)); and second, Apoptin-induced cell death is not dependent upon the p53 tumor suppressor (Danen-Van Oorschot et al., Proc. Natl. Acad. Sci., 94:5843-5847 (1997); Danen-Van Oorschot et al., Adv. Exp. Med. Biol., 457:245-249 (1999).). Thus, Apoptin represents a potential agent for the treatment of tumors that have lost their p53 status and are therefore refractory to many cancer therapies. Apoptin has shown efficacy in treating human xenografted tumors in mice and is currently being evaluated as a gene therapy agent to selectively destroy cancer cells (van der Eb et al., Cancer Gene Ther., 9:53-61 (2002)).

Apoptin contains no obvious functional motifs and has no homology with other proteins that would help elucidate its function. It does contain a canonical nuclear exportation signal (NES), and the subcellular location of Apoptin appears to be important for its activity: in normal cells, Apoptin is found predominantly in the cytoplasm, whereas in transformed and malignant cells it is located in the nucleus. The mechanism by which Apoptin differentially localizes to the nucleus in normal versus transformed cells is unknown, and whether this re-localization is critical for its apoptotic activity has not been determined. In addition, the molecular pathway by which Apoptin induces apoptosis has not been characterized.

SUMMARY

The invention is based, in part, on the discovery of domains of Apoptin that are required for its nuclear localization and association with the cytoskeleton, and that Apoptin associates with anaphase promoting complex subunit 1 (APC1) and inhibits APC1, inducing G2/M arrest and apoptosis. One theory, not meant to be limiting, is that Apoptin causes APC1 to dissociate from the anaphase promoting complex/cyclosome (APC/C). Generally, the invention provides methods of identifying compounds that modulate apoptosis by inhibiting APC1, e.g., by causing APC1 to dissociate from the APC/C and initiating apoptosis. The invention further provides methods of treating disease by administering such compounds.

Provided herein are methods of identifying candidate compounds that induce apoptosis. The methods include obtaining a sample including anaphase promoting complex subunit 1 (APC1), which is a subunit of the anaphase promoting complex/cyclosome (APC/C); in some embodiments, the sample includes APC/C (e.g., the whole complex, i.e., subunits 1-11 of the APC/C, in a functional complex); in some embodiments, the sample also includes cdc20 activator protein. The sample is contacted with a test compound, under conditions that enable the test compound to interact with the APC1. In some embodiments, the sample is an in vitro sample, e.g., a substantially pure sample of APC1 or APC/C in a suitable buffer. In some embodiments, the sample comprises a cell-free extract comprising APC1 or APC/C. An interaction of the test compound with APC1 (or APC/C) is then evaluated, and test compounds that interact with APC1 can be considered candidate compounds that induce apoptosis. Evaluating an interaction of the test compound with APC1 can include evaluating binding of the test compound to APC1; a test compound that binds to APC1 is a candidate compound that modulates apoptosis. Evaluating an interaction of the test compound with APC1 can also or alternatively include evaluating an effect of the test compound on a function of APC1. A test compound that modulates an APC1 function can be considered a candidate compound that modulates apoptosis. Functions of APC1 that can be evaluated include ubiquitination of a target protein, e.g., a cell cycle protein, e.g., one or more of Clb5, Cdc20, Cdh1, cyclin B1, Plk1, and securin. See, e.g., Peters et al., Mol. Cell, 9:931-943 (2002), for additional information regarding the functions of APC1. Finally, association of APC1 with APC/C can be evaluated, and a test compound that causes dissociated of APC1 from APC/C (e.g., causes APC1 that is already associated with APC/C to become dissociated, or prevents unassociated APC1 from associating with APC/C) can be considered a candidate compound that modulates apoptosis.

The methods can further include contacting the candidate compound with a population of viable cells, e.g., primary or cultured cell, or transformed or non-transformed cells, to evaluate the ability of the compound to induce apoptosis.

Also described herein are methods for identifying candidate therapeutic compounds for the treatment of a condition associated with aberrant (e.g., increased or decreased) apoptosis. The methods include providing a model of the condition, e.g., an animal (in vivo) or cell (in vitro) model of the condition. The model is contacted with a candidate compound that causes anaphase promoting complex subunit 1 (APC1) to dissociate from anaphase promoting complex/ cyclosome (APC/C), e.g., a candidate compound identified by a method described herein. An effect of the candidate compound on the rate of apoptosis in the model is evaluated, and a candidate compound that modulates the rate of apoptosis in the model is considered a candidate therapeutic compound for the treatment of the condition.

Conditions associated with decreased apoptosis can be, e.g., disorders associated with increased cellular proliferation, e.g., cancer or psoriasis. Conditions associated with increased apoptosis include degenerative diseases, e.g., amyotrophic lateral sclerosis (ALS), Parkinson's disease, Alzheimer's disease, ischemic brain injury, Huntington's disease, Glaucoma, Age-related macular degeneration (AMD), peripheral neuropathy, stroke, depression, Diamond-Blackfan Anemia (DBA), Fanconi Anemia (FA) Shwachman Diamond Syndrome (SDS), and virus induced lymphocyte depletion (e.g., associated with HIV/AIDS).

In some embodiments, the test compound is a nucleic acid encoding an active fragment of Apoptin; an APC1-specific antisense, siRNA, ribozyme, or aptamer; or an active fragment of Apoptin (e.g., comprising SEQ ID NO:16 or SEQ ID NO:17).

In addition, described herein are methods for inducing apoptosis in a cell expressing anaphase promoting complex/cyclosome (APC/C), wherein the APC/C includes anaphase promoting complex subunit 1 (APC1). The methods include contacting the cell with a compound that causes the dissociation of APC1 from APC/C, thereby inducing apoptosis.

Also provided herein are methods of treating a subject who has a condition associated with aberrant apoptosis, by administering to the subject a therapeutically effective amount of a compound that inhibits a function of APC1, e.g., a compound identified by a method described herein.

Methods of preparing therapeutic compositions for the treatment of conditions associated with decreased apoptosis are also described herein. Generally, the methods include formulating a candidate therapeutic compound identified by a method described herein (e.g., a nucleic acid encoding an active fragment of Apoptin; an APC1-specific antisense, siRNA, ribozyme, or aptamer; or an active fragment of Apoptin (e.g., comprising SEQ ID NO:16 or SEQ ID NO:17)) in a pharmaceutically acceptable carrier.

As used herein, an "active fragment of Apoptin" is a peptide that includes less than the full-length of native or wild-type Apoptin, but retains APC1 binding activity and the ability to induce apoptosis, with at least 35% of the efficacy of the full-length Apoptin polypeptide. In some embodiments, the active fragment includes all or part of the C-terminus of Apoptin, e.g., amino acids 42-121 (SEQ ID NO: 16) or 82-121 (SEQ ID NO: 17) of Apoptin. In some embodiments, the active fragment is part of a fusion protein with another protein, e.g., a non-Apoptin protein, e.g., a TAT protein transduction domain (PTD).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 6 is a reproduction of three gels demonstrating that Apoptin expression does not affect mRNA levels of APC/C substrates. RT-PCR analysis of cyclin B1 (top) or Plk (middle) mRNA levels in H1299 cells 24 hours following infection with Ad-Apwt or Ad-LacZ, or in cells treated with nocodozole (noc) for 12 hours. GAPDH was monitored as a loading control (bottom).

FIG. 7 is an immunoblot showing that Caspase-3 is activated in APC1 siRNA-transfected cells. Whole cell extracts from H1299 cells transfected with siRNAs directed against either Lamin A/C (left column) or APC1 (right column) were analyzed by immunoblotting with a monoclonal antibody against human caspase-3. Caspase-3 activation was determined by cleavage of pro-caspase-3 (32 kDa) to the activated form (17 kDa). Tubulin was monitored as a loading control (bottom row).

FIG. 8 is the nucleotide sequence of Apoptin (SEQ ID NO:2). The region of the Chicken anemia virus genome (GenBank Accession number: NC_001427) that encodes Apoptin is 486-851, which has been renumbered here as 1-366.

FIG. 9A-B is the nucleotide sequence of Homo sapiens anaphase promoting complex subunit 1 (APC1) mRNA (GenBank Accession number: NM_022662) (SEQ ID NO:15).

DETAILED DESCRIPTION

Figure 1A:
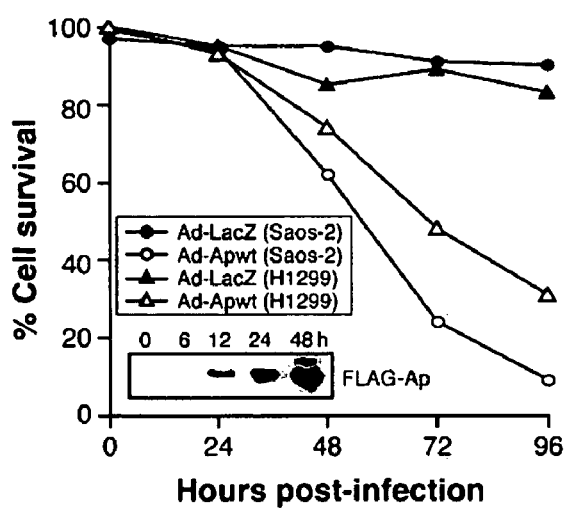
FIG. 1A is a line graph showing cell survival rates in Saos-2 (filled and open circles) and H1299 cells (filled and open triangles) infected with adenovirus expressing a FLAG-tagged wild type Apoptin (Ad-Apwt; open circles and triangles) or LacZ (Ad-LacZ; filled circles and triangles); cell death was monitored for 96 hours post-infection by trypan blue exclusion. The inset shows the results of immunoblot analysis using an anti-FLAG antibody to monitor Apoptin protein expression in Saos-2 cells at 0, 6, 12, 24, and 48 hours post infection.

The majority of human cancers lack the tumor suppressor p53; this increases their resistance to conventional chemotherapeutic agents that exert their cytotoxic effects through p53-mediated apoptosis (Hussain and Harris, Cancer Res., 58:4023-4037 (1998); Beroud and Soussi, Hum. Mutat., 21:176-181 (2003)). It is therefore critical to identify and characterize novel p53-independent apoptotic pathways. The results described herein indicate that Apoptin, which exerts its influence primarily through non-p53 dependent pathways, induces G2/M arrest and apoptosis in p53-null transformed cells through association with and inhibition of the APC/C (anaphase promoting complex/cyclosome), by causing the dissociation of anaphase promoting complex subunit 1 (APC1) from the APC/C. Thus, the invention provides methods of identifying compounds that mimic the action of Apoptin on APC1, such compounds, and methods of using them.

The molecular mechanism by which Apoptin induces cell death has been unknown. As described herein, two experimental approaches were used to identify the mechanism by which Apoptin induces cell death. To delineate the mechanism of differential localization of Apoptin in normal versus transformed cells, elements within Apoptin have been identified that are required for localization of the protein. In addition, cellular factor(s) that are required for Apoptin localization have been identified. To identify factors involved in the apoptotic pathway, a co-immunoprecipitation approach was used to identify proteins that interact with Apoptin in vivo as an Apoptin-binding protein. APC-1 was identified by these methods as an Apoptin-binding protein. Thus, the invention includes methods of identifying Apoptin-binding proteins and APC1-binding regions of Apoptin.

APC1 is thought to be essential for assembly and regulation of the cyclosome complex (Kraft et al., EMBO J., 22:6598-6609 (2003); Vodermaier et al., Curr. Biol., 13:1459-1468 (2003)). The preparative immunoprecipitation/mass spectroscopic analysis described herein identified APC1, but not other APC/C subunits (FIG. 1C), suggesting that Apoptin associates with free APC1 and not the intact cyclosome complex. Furthermore, gel filtration analysis suggested that in the presence of Apoptin, APC1 dissociates from the APC/C, resulting in disruption of the complex and loss of APC/C activity. Interestingly, subunits of the APC/C, including APC1, have been shown to localize to the active centromere of dicentric chromosomes (Saffery et al., Hum. Genet., 107:376-384 (2000)). Thus, the association of Apoptin with α- and β-tubulin described herein may result from an interaction between Apoptin and the spindle complex.

Described herein are methods for identifying compounds that mimic the apoptosis-inducing action of Apoptin on APC1, or otherwise modulate a function of APC1. Compounds that inhibit a function of APC1 are useful for promoting apoptosis (e.g., in cancer cells). Also described herein are methods of treating a subject having a disorder characterized by aberrant (e.g., decreased or increased) apoptotic processes, by administering a compound that modulates a function of APC1. For example, introduction of active fragments of Apoptin (e.g., APC1-binding fragments) into a cell is a method of inducing apoptosis. Also included are compounds identified by the methods described herein.

Screening Methods

The new methods of identifying compounds that induce apoptosis identify compounds that interact with and inhibit a function of APC1. A function of APC1 can include association with the APC/C, or ubiquitination of a target protein, e.g., a cell cycle protein such as Clb5, Cdc20, Cdh1, cyclin B1, Plk1, or securing.

In some embodiments, the test compounds bind to an APC1 polypeptide or nucleic acid, e.g., mRNA, and cause a decrease in levels of APC1 polypeptide.

These methods can be used to identify test compounds that inhibit APC1 function. In some embodiments, the methods include determining whether a compound can bind to APC1 and cause the dissociation of APC1 from the APC/C.

In some embodiments, the methods include determining whether a compound that is known to bind to APC1 also inhibits APC1 function, e.g., inhibit the ability of APC1 to ubiquitinate a target protein, and/or cause the dissociation of APC1 from the APC/C.

In some embodiments, the methods include providing one or more samples that include both APC1 and one or more test compounds, e.g., Apoptin polypeptides, or active fragments of one or both of them, e.g., APC1 or Apoptin. An "active fragment" is a fragment that retains the ability to bind the other protein, e.g., an active fragment of Apoptin retains the ability to bind APC1; examples include the deletion mutants Ap(42-121) (SEQ ID NO: 16), which includes amino acids 42-121 of Apoptin, and Ap(82-121) (SEQ ID NO: 17), which includes amino acids 82-121 of Apoptin, as described herein; other active fragments can be easily identified and prepared by one of ordinary skill in the art. Active fragments of apoptin that bind APC1 and induce apoptosis can be considered to mimic the action of Apoptin on APC1. In some embodiments, the methods include providing samples including cells that express APC1, and evaluating the effect of a test compound on the level or activity of APC1 in the cells. In some embodiments, the samples include APC1 and additional components of the APC/C, e.g., the whole thing, i.e., subunits 1-11 in complex as well as cdc20 activator protein. In particular, assays for test compounds that affect the function of APC1 will include additional components of the APC/C.

In some embodiments, the methods include determining the subcellular localization of Apoptin or a fragment thereof.

A number of suitable assay methods to detect binding of test compounds to APC1 are known in the art and described herein, and include, but are not limited to, surface plasmon resonance (SPR)/Biacore™, fluorogenic binding assays, fluid phase binding assays, affinity chromatography, size exclusion or gel filtration, ELISA, immunoprecipitation, competitive binding assays, gel shift assays, and mass spectrometry based methods, inter alia.

In some embodiments, methods described herein include a first screen for compounds that bind to APC1. Compounds that are identified as binding to APC1 can then be used in a second screen to identify those compounds that inhibit a function of APC1. Alternatively, the first screen can be omitted and the compounds can simply be screened for their ability to inhibit a function of APC1, e.g., to inhibit the ubiquitin ligase function of APC1 or to cause the dissociation of APC1 from the APC/C, e.g., by identifying those compounds that cause a decrease in ubiquitination of an APC1 target protein, e.g., Clb5, Cdc20, Cdh1, cyclin B1, Plk1, and/or securin, or an increase in free APC1 in a sample of APC/C. For example, APC/C complex could be purified to near homogeneity from xenopus extracts (among other sources) using an anti-APC3 antibody that will immunoprecipitate APC/C subunits 1-11 in a functional complex to be used in in vitro experiments. Such experiments could test the function of the APC/C to ubiquitinate known substrates, such as mitotic cyclins, in a ubiquitination assay involving radiolabled ubiquitin and a laddering assay. Such experiments are routine in the art.

Once a compound that inhibits an action of APC1 is identified, the compound can be considered a candidate compound that induces apoptosis. The ability of such compounds to induce apoptosis can be evaluated in a population of viable cells or in an animal, e.g., an animal model. A number of methods are known in the art and described herein for measuring apoptosis and rates of apoptosis, e.g., trypan blue exclusion.

Such compounds are useful, e.g., as candidate therapeutic compounds for the treatment of conditions associated with decreased apoptosis. Thus, included herein are methods for screening for candidate therapeutic compounds for the treatment of conditions associated with decreased apoptosis, as described herein. The methods include administering the compound to a model of the condition, e.g., contacting a cell (in vitro) model with the compound, or administering the compound to an animal model of the condition, e.g., an animal model of a condition associated with decreased apoptosis such as cancer. The model is then evaluated for an effect of the candidate compound on the rate of apoptosis in the model, and a candidate compound that increases the rate of apoptosis in the model can be considered a candidate therapeutic compound for the treatment of the condition. Such effects can include clinically relevant effects such as decreased tumor size or decreased tumor growth rate; decreased metastatic involvement or decreased rate of metastasis; decreased pain; increased life span; and so on. Such effects can be determined on a macroscopic or microscopic scale. Methods such as those described in van der Eb et al., Cancer Gene Ther., 9:53-61 (2002), can be used.

Candidate therapeutic compounds identified by these methods can be further verified, e.g., by administration to human subjects in a clinical trial.

Test Compounds

The test compounds utilized in the assays and methods described herein can be, inter alia, nucleic acids, small molecules, organic or inorganic compounds, antibodies or antigen-binding fragments thereof, polynucleotides, peptides, or polypeptides. For example, Apoptin or APC1 polypeptides or polynucleotides (e.g., Apoptin or APC1 polypeptide variants including truncation mutants, deletion mutants, and point mutants; nucleic acids including sense, antisense, aptamers, and small inhibitory RNAs (siRNAs) including short hairpin RNAs (shRNAs) and ribozymes) can be used as test compounds in the methods described herein. Alternatively, compounds or compositions that mimic the APC1-binding portion of Apoptin can be used. A test compound that has been screened by an in vitro method described herein and determined to have a desired activity, e.g., binding of Apoptin to APC1 causing the subsequent dissociation of APC1 from APC/C, can be considered a candidate compound. A candidate compound that has been screened, e.g., in an in vitro or in vivo model, and determined to have a desirable effect on one or more symptoms of a disorder associated with decreased apoptosis, can be considered a candidate therapeutic agent. Candidate therapeutic agents, once screened in a clinical setting, are therapeutic agents, and both types of agents can be optionally optimized (e.g., by derivatization), and formulated with pharmaceutically acceptable excipients or carriers to form pharmaceutical compositions.

Small Molecules

Small molecule test compounds can initially be members of an organic or inorganic chemical library. As used herein, "small molecules" refers to small organic or inorganic molecules of molecular weight below about 3,000 Daltons. The small molecules can be natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio., 1:60 (1997). In addition, a number of small molecule libraries are commercially available.

The test compound can have a structure that is based on an active fragment of Apoptin. For example, computer modeling methods known in the can be used to rationally design a molecule that has a structure similar to an active fragment of Apoptin, or an APC1-binding portion thereof.

In some embodiments, the compounds are optimized to improve their therapeutic index, i.e., increase therapeutic efficacy and/or decrease unwanted side effects. Thus, in some embodiments, the methods described herein include optimizing the test or candidate compound. In some embodiments, the methods include formulating a therapeutic composition including a test or candidate compound (e.g., an optimized compound) and a pharmaceutically acceptable carrier. In some embodiments, the compounds are optimized by derivatization using methods known in the art.

Polynucleotides

In some embodiments, the test compound comprises a polynucleotide that encodes Apoptin or APC1, or an active fragment thereof. In some embodiments, the compound is a polynucleotide that encodes an active fragment of Apoptin that retains APC1 binding activity, e.g., all or part of the C-terminus of Apoptin, e.g., amino acids 42-121 (SEQ ID NO: 16) or 82-121 (SEQ ID NO: 17) of Apoptin (Genbank Accession No. NP_056774, encoded by nucleotides 486-851 of NC_001427; the region of the Chicken anemia virus genome that encodes Apoptin is 486-851 (SEQ ID NO:2).

Sense Nucleic Acids

In some embodiments, the test compound comprises a polynucleotide that encodes a polypeptide that is at least about 85% identical to the amino acid sequence of Apoptin (SED ID NO:1). In some embodiments, the polynucleotide encodes a polypeptide that is at least about 90%, 95%, 99%, or 100% identical to the full length sequence of Apoptin described herein (e.g., SEQ ID NO:1), or an active fragment thereof. In some embodiments, the polynucleotide encodes a peptide fragment of SEQ ID NO:1, e.g., an active fragment thereof that retains the ability to bind APC1, and modulate APC1 function, e.g., cause APC1 to dissociate from the APC/C. In some embodiments, the active fragment is at least about 10, 12, 14, 16, 18, 20, 22, 24, 26, 28, 30, 32, 34, 36, 38, 39, 40, 45, 50, 55, 60, 65, 70, 75, 80 or more amino acids long. In some embodiments, the polynucleotide is, or is complementary to, SEQ ID NO:2 or a portion thereof that encodes an active fragment of Apoptin, e.g., a fragment comprising SEQ ID NO:16 or 17. The nucleic acid can include one or more noncoding regions of the coding strand of a nucleotide sequence encoding Apoptin (e.g., the 5' and 3' untranslated regions). A number of methods are known in the art for obtaining suitable nucleic acids, see, e.g., Sambrook et al., *Molecular Cloning: A Laboratory Manual* (Cold Spring Harbor Laboratory, Cold Spring Harbor, N.Y.; 3rd ed. 2001).

RNA Interference (RNAi)

RNAi is a remarkably efficient process whereby double-stranded RNA (dsRNA, also referred to herein as siRNAs, for small interfering RNAs, or ds siRNAs, for double-stranded small interfering RNAs) induces the sequence-specific degradation of homologous mRNA in animals and plant cells (Hutvagner and Zamore, Curr. Opin. Genet. Dev., 12:225-232 (2002); Sharp, Genes Dev., 15:485-490 (2001)). In mammalian cells, RNAi can be triggered by duplexes of small interfering RNA (siRNA) (Chiu et al., Mol. Cell., 10:549-561 (2002); Elbashir et al., Nature, 411:494-498 (2001)), or by micro-RNAs (miRNA), functional small-hairpin RNA (shRNA), or other dsRNAs which are expressed in vivo using DNA templates with RNA polymerase III promoters (Zeng et al., Mol. Cell, 9:1327-1333 (2002); Paddison et al., Genes Dev., 16:948-958 (2002); Lee et al., Nature Biotechnol., 20:500-505 (2002); Paul et al., Nature Biotechnol., 20:505-508 (2002); Tuschl, T., Nature Biotechnol., 20:440-448 (2002); Yu et al., Proc. Natl. Acad. Sci. USA, 99(9):6047-6052 (2002); McManus et al., RNA, 8:842-850 (2002); Sui et al., Proc. Natl. Acad. Sci. USA, 99(6):5515-5520 (2002)).

The methods described herein can include the use of dsRNA molecules that are targeted to (i.e., bind to) APC1 mRNA. The dsRNA molecules typically comprise 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is identical or substantially identical to the first strand. Each strand can also have one or more overhanging (i.e., non-complementary) nucleotides, e.g., one, two, three, four or more overhanging nucleotides, e.g., dTdTdT.

The dsRNA molecules can be chemically synthesized, or can be transcribed in vitro from a DNA template, or in vivo from, e.g., shRNA. The dsRNA molecules can be designed using any method known in the art; a number of algorithms are known in the art, see, e.g., Tuschl et al., Genes Dev 13(24):3191-7 (1999), and many are available on the internet, e.g., on the websites of Dharmacon (Lafayette, Colo.) or Ambion (Austin, Tex.).

Negative control siRNAs should have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

micro RNA (miRNAs) of approximately 22 nucleotides can be used to regulate gene expression at the post transcriptional or translational level. miRNAs can be excised in the cell from an approximately 70 nucleotide precursor RNA stem-loop by Dicer, an RNase III-type enzyme, or a homolog thereof. By substituting the stem sequences of the miRNA precursor with miRNA sequence complementary to the target mRNA, a vector construct that expresses the novel miRNA can be used to produce siRNAs to initiate RNAi against specific mRNA targets in mammalian cells (Zeng (2002), supra). When expressed by DNA vectors containing polymerase III promoters, micro-RNA designed hairpins can silence gene expression (McManus (2002), supra).

dsRNA can be delivered directly into cells in vivo or in vitro using methods known in the art, e.g., cationic liposome transfection, nanoparticles, and electroporation, or expressed in vivo or in vitro from recombinant DNA constructs that allow longer-term target gene suppression in cells, including mammalian Pol III promoter systems (e.g., H1 or U6/snRNA promoter systems (Tuschl (2002), supra) capable of expressing functional double-stranded siRNAs; (Bagella et al., *J. Cell. Physiol.* 177:206-213 (1998); Lee et al. (2002), supra; Miyagishi et al. (2002), supra; Paul et al. (2002), supra; Yu et al. (2002), supra; Sui et al. (2002), supra). Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002), supra). Transcriptional termination by RNA Pol III occurs at runs of four consecutive T residues in the DNA template, providing a mechanism to end the siRNA transcript at a specific sequence. The dsRNA thus produced is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence under the control of T7 promoter also make functional siRNAs when cotransfected into cells with a vector expression T7 RNA polymerase (Jacque (2002), supra).

In an animal, whole-embryo electroporation can efficiently deliver synthetic siRNA into post-implantation mouse embryos (Calegari et al., *Proc. Natl. Acad. Sci. USA,* 99(22): 14236-40 (2002)). In adult mice, efficient delivery of siRNA can be accomplished by "high-pressure" delivery technique, a rapid injection (within 5 seconds) of a large volume of siRNA containing solution into animal via the tail vein (Liu (1999), supra; McCaffrey (2002), supra; Lewis, *Nature Genetics* 32:107-108 (2002)). Local delivery can also be used, e.g., with a carrier such as lipiodol (iodine in oil) to facilitate delivery into cells.

Engineered RNA precursors, introduced into cells or whole organisms as described herein, can be used for the production of a desired siRNA molecule. Such an siRNA molecule can then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the protein encoded by that mRNA in the cell or organism. Additional information regarding the use of RNAi can be found in *RNA Interference Editing, and Modification: Methods and Protocols* (*Methods in Molecular Biology*), Gott, Ed. (Humana Press, 2004);

Antisense Polynucleotides

An "antisense" nucleic acid can include a nucleotide sequence that is complementary to a "sense" nucleic acid encoding a protein, e.g., complementary to all or a portion of the coding strand of a double-stranded cDNA molecule or complementary to APC1 mRNA sequence. In another embodiment, the antisense nucleic acid molecule is antisense to a "noncoding region" of the coding strand of a nucleotide sequence encoding APC1 (e.g., the 5' and 3' untranslated regions). An antisense polynucleotide statistically significantly inhibits the expression of the target gene.

Based upon the sequences disclosed herein, one of skill in the art can easily choose and synthesize any of a number of appropriate antisense molecules for use in accordance with the present invention. For example, a "gene walk" comprising a series of oligonucleotides of 15-30 nucleotides spanning the length of an APC1 nucleic acid can be prepared, followed by testing for inhibition of APC1 expression. Optionally, gaps of 5-10 nucleotides can be left between the oligonucleotides to reduce the number of oligonucleotides synthesized and tested. Other methods, including computational analysis, RNAse H mapping, and antisense-oligonucleotide scanning microarrays, can also be used (see, e.g., *DNA Microarrays: A Practical Approach,* Schena, Ed. (Oxford University Press 1999; Scherr and Rossi, *Nuc. Acids Res.,* 26(22):5079-5085 (1998)).

An antisense nucleic acid can be designed such that it is complementary to the entire coding region of a target APC1 mRNA (NM_022662; SEQ ID NO:2), but can also be an oligonucleotide that is antisense to only a portion of the coding or noncoding region of the target mRNA. For example, the antisense oligonucleotide can be complementary to a region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Antisense nucleic acid molecules are typically administered to a subject (e.g., by direct injection at a tissue site), or generated in situ such that they hybridize with or bind to cellular mRNA and/or genomic DNA encoding an APC1 protein to thereby inhibit expression of the protein, e.g., by inhibiting transcription and/or translation.

Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter can be used.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., *Nucleic Acids. Res.* 15:6625-6641 (1987)). The antisense nucleic acid molecule can also comprise a 2'-o-methylribonucleotide (Inoue et al. *Nucleic Acids Res.* 15:6131-6148 (1987)) or a chimeric RNA-DNA analogue (Inoue et al. *FEBS Lett.,* 215:327-330 (1987)).

APC1 gene expression can be inhibited by targeting nucleotide sequences complementary to the regulatory region of APC1 (e.g., the APC1 promoter and/or enhancer) to form triple helical structures that prevent transcription of the Spt5 gene in target cells. See generally, Helene, *Anticancer Drug Des.* 6:569-84 (1991); Helene, *Ann. N.Y. Acad. Sci.* 660:27-36 (1992); and Maher, *Bioassays* 14:807-15 (1992). The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Ribozymes

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for an APC1-encoding nucleic acid can include one or more sequences complementary to the nucleotide sequence of an APC1 cDNA disclosed herein, and a sequence having known catalytic sequence responsible for mRNA cleavage (see U.S. Pat. No. 5,093,246 or Haselhoff and Gerlach, *Nature*, 334:585-591 (1988)). For example, a derivative of a Tetrahymena L-19 IVS RNA can be constructed in which the nucleotide sequence of the active site is complementary to the nucleotide sequence to be cleaved in an Apoptin- or APC1-encoding mRNA. See, e.g., Cech et al., U.S. Pat. No. 4,987,071; and Cech et al., U.S. Pat. No. 5,116,742. Alternatively, Apoptin or APC1 mRNA can be used to select a catalytic RNA having a specific ribonuclease activity from a pool of RNA molecules. See, e.g., Bartel, and Szostak, *Science*, 261:1411-1418 (1993).

Peptides/Polypeptides

In some embodiments, the test compound includes an Apoptin or APC1 polypeptide, or an active fragment thereof. In some embodiments, the compound is an active fragment of Apoptin that retains APC1 binding activity, e.g., all or part of the C-terminus of Apoptin, e.g., amino acids 42-121 (SEQ ID NO: 16) or 82-121 (SEQ ID NO: 17) of Apoptin (SEQ ID NO:1; Genbank Accession No. NP_056774, encoded by nucleotides 486-851 of NC_001427). The region of the Chicken anemia virus genome that encodes Apoptin is 486-851 (SEQ ID NO:2).

The amino acid sequence of the Apoptin polypeptide is as follows:

thereof, e.g., fluorescent proteins such as green fluorescent protein (GFP), red fluorescent protein (RFP), blue fluorescent protein (BFP) or yellow fluorescent protein (YFP), or peptides that enhance delivery, e.g., a TAT protein transduction domain (PTD) as described herein.

Pharmaceutical Compositions and Methods of Administration

The invention includes compounds that mimic an action of Apoptin on APC1, identified by a method described herein. In some embodiments, the compound is a protein, nucleic acid, small molecule, peptide, siRNA, ribozyme, antisense oligonucleotide or antibody, e.g., that binds specifically to an APC1 nucleic acid or protein and inhibits APC1 function, e.g., by degrading APC1 or promoting dissociation of APC1 from the APC/C. In some embodiments, the compound is an active fragment of Apoptin that retains APC1 binding activity, e.g., all or part of the C-terminus of Apoptin, e.g., amino acids 42-121 (SEQ ID NO: 16) or 82-121 (SEQ ID NO:17) of Apoptin (NP_056774; SEQ ID NO:1). In some embodiments, the compound has a structure that is similar to an active fragment of Apoptin.

Methods of Formulation

The compounds described herein can be incorporated into pharmaceutical compositions. Such compositions typically include the active ingredient and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The

```
                                                                        (SEQ ID NO:1)
  1 MNALQEDTPP GPSTVFRPPT SSRPLETPHC REIRIGIAGI TITLSLCGCA NARAPTLRSA

61 TADNSESTGF KNVPDLRTDQ PKPPSKKRSC DPSEYRVSEL KESLITTTPS RPRTAKRRIR

121 L
```

In some embodiments, the test compound comprises a polypeptide that is at least about 85% identical to the amino acid sequence of SED ID NO:1. In some embodiments, the polypeptide is at least about 90%, 95%, 99%, or 100% identical to the full length sequence of Apoptin described herein (e.g., SEQ ID NO:1), or an active fragment thereof. In some embodiments, the active fragment is at least about 10, 12, 14, 16, 18, 20, 22, 24, 26, 28, 30, 32, 34, 36, 38, 39, 40, 45, 50, 55, 60, 65, 70, 75, 80 or more amino acids long. In some embodiments, the active fragment includes SEQ ID NO:16 or 17. A "polypeptide comprising an active fragment of Apoptin" includes less than the full length of SEQ ID NO:1, but can include other (i.e., non-Apoptin) proteins or fragments parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from pressured container or dispenser which contains a suitable propellant, e.g., a gas such as carbon dioxide, or a nebulizer. Such methods include those described in U.S. Pat. No. 6,468,798. Compositions for inhalation can also include propellants, surfactants, and other additives, e.g., to improve dispersion, flow, and bioavailability.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Compounds comprising nucleic acids can also be administered by transfection or infection using methods known in the art, including but not limited to the methods described in McCaffrey et al. (2002), *Nature*, 418(6893), 38-9 (hydrodynamic transfection); Xia et al. (2002), *Nature Biotechnol.*, 20(10), 1006-10 (viral-mediated delivery); or Putnam (1996), *Am. J. Health Syst. Pharm.*, 53(2), 151-160, erratum at *Am. J. Health Syst. Pharm.*, 53(3), 325 (1996). Compounds comprising nucleic acids can also be administered by method suitable for administration of DNA vaccines. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), *Clin. Immunol. Immunopathol.*, 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the compounds are prepared with carriers that will protect the active ingredient against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In some embodiments, the compounds (e.g., polypeptides) are modified to enhance delivery into cells, e.g., by the addition of an optimized or native TAT protein transduction domain (PTD), e.g., as described in Ho et al., Cancer Res. 61(2):474-7 (2001). Where the compound is a polypeptide, the polypeptide can be a fusion protein comprising an active portion (e.g., an active fragment of Apoptin) and a TAT PTD fused in frame.

The pharmaceutical compositions can be included in a container, pack, or dispenser together with instructions for administration.

Methods of Treatment

As used herein, the term "treatment" is defined as the application or administration of a therapeutic agent described herein, or identified by a method described herein, to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

Examples of routes of administration include parenteral, e.g., intravenous, intradermal, subcutaneous, oral (e.g., inhalation), transdermal (topical), transmucosal, and rectal administration.

Therapeutic agents include, for example, proteins, nucleic acids, small molecules, peptides, antibodies, siRNAs, ribozymes, and antisense oligonucleotides. Dosage, toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a compound (i.e., an effective dosage) means an amount sufficient to produce a therapeutically (e.g., clinically) desirable result; the exact nature of the result will vary depending on the nature of the disorder being treated. For example, where the disorder to be treated is a degenerative disorder, the result can be a cessation of cellular degeneration, or a reduction in the rate of cellular degeneration. Where the disorder is associated with increased cellular proliferation, the result can be a cessation of or decrease in cellular proliferation. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments.

The present invention provides for both prophylactic and therapeutic methods of treating a subject at risk of (or susceptible to) a disorder or having a disorder associated with aberrant cellular apoptosis. Thus, included herein are methods for treating disorders associated with aberrant (abnormally increased or decreased) apoptotic processes. These include disorders associated with decreased apoptotic processes, e.g., cellular proliferative disorders or cellular differentiative disorders, e.g., cancer, autoimmune disorders, or psoriasis, and disorders associated with increased apoptosis, e.g., degenerative disorders (including neurodegenerative disorders such as Alzheimer's Disease, amyotrophic lateral sclerosis (ALS), Parkinson's disease, Alzheimer's disease, ischemic brain injury, and Huntington's disease), Glaucoma, Age-related macular degeneration (AMD), peripheral neuropathy, stroke, depression, Diamond-Blackfan Anemia (DBA), Fanconi Anemia (FA) Shwachman Diamond Syndrome (SDS), ischemic injury (myocardial infarction), and virus induced lymphocyte depletion (e.g., associated with HIV/AIDS).

Cellular Proliferative Disorders

Compounds that inhibit APC1 are useful in the treatment of disorders associated with abnormally decreased apoptotic processes, e.g., cellular proliferative disorders or cellular differentiative disorders, e.g., cancer, e.g., by inducing apoptosis in those cells. Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer," "hyperproliferative," and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. In some embodiments, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, Crit Rev. in Oncol./Hemotol., 11:267-97 (1991)); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Other examples of proliferative and/or differentiative disorders include skin disorders. The skin disorder may involve the aberrant activity of a cell or a group of cells or layers in the dermal, epidermal, or hypodermal layer, or an abnormality in the dermal-epidermal junction.

Examples of skin disorders include psoriasis, psoriatic arthritis, dermatitis (eczema), e.g., exfoliative dermatitis or atopic dermatitis, pityriasis rubra pilaris, pityriasis rosacea, parapsoriasis, pityriasis lichenoiders, lichen planus, lichen nitidus, ichthyosiform dermatosis, keratodermas, dermatosis, alopecia greata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as atopic dermatitis, allergic dermatitis, seborrheic dermatitis or solar dermatitis; keratoses such as seborrheic keratosis, senile keratosis, actinic keratosis, photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; lichen planus; and keratitis.

Viral Infections

The adenovirus protein E4orf4 also arrests cells in G2/M (Kornitzer et al., J. Cell Biol., 154:331-344 (2001)) and induces apoptosis in the absence of p53 (Marcellus et al, J. Virol., 72: 7144-7153 (1998)). Yeast genetics experiments suggest that this E4orf4-induced cell cycle arrest is mediated by the APC/C, most likely through its Cdc16 subunit (Kornitzer et al., 2001, supra). Therefore, inhibition of the cyclosome complex may represent a convergently-evolved viral cytopathic mechanism. Arresting cells in mitosis may facilitate viral replication. For example, mitotic cells become rounded and lift from the surrounding substrate, which may provide a means whereby infected cells become capable of moving to uninfected areas to more efficiently disseminate virus.

Methods of Treatment

To treat disorders associated with decreased apoptosis, e.g., cellular proliferative and/or differentiative disorders, apoptosis can be induced by mimicking an Apoptin/APC1 interaction, e.g., by administering an agent that inhibits APC1 as described herein, e.g., an active fragment of Apoptin as described herein. To treat disorders associated with increased apoptosis, e.g., as described herein, apoptosis can be inhibited by administering an agent that enhances APC1 function, e.g., identified by a method described herein.

The invention is further described in the following examples, which do not limit the scope of the invention described in the claims.

EXAMPLES

Example 1

Adenovirus and Plasmid Construction

Apoptin adenovirus (Ad-Apwt) containing a single 5' FLAG epitope was generated using the AdEasy XL Adenoviral Vector System (Stratagene) according to the manufacturer's instructions. Viral supernatants were plaque purified, amplified, and titers determined by plaque assay. LacZ adenovirus (Ad-LacZ) was prepared as previously described (Bacchetti and Graham. Int. J. Onc., 3:781-788 (1993)). Cells were infected at approximately 80% confluence at an MOI of 35. FLAG-Apoptin deletion mutants were constructed by PCR amplification of truncated Apoptin sequences, which were directionally cloned into the vector p3XFLAG-myc-CMV-26 (Sigma) to construct an in-frame N-terminal fusion to the FLAG epitopes. Stop sequences were generated to exclude the C-terminal myc tag. N-terminal tagged GFP fusion deletion mutants were subcloned from the FLAG-deletion library. All clones were confirmed by restriction digest analysis and DNA sequencing.

The GFP-Ap-pmNES, -pmNLS and -pmNLS2 constructs were generated by PCR site-directed mutagenesis. DsRed-Apoptin fusions were generated by PCR amplification of GFP-Apoptin templates Apwt, Ap-pmNES and Ap(82-121) followed by cloning into pDsRed1-N1 (Clontech) via engineered EcoRI-BamHI restriction sites. For the dsRed-Ap(82-121) construct, a start codon was added because the endogenous Apoptin 5' sequence had been removed. The GFP-Ap-RevNES construct was generated by replacing the wild type Apoptin NES sequence with an oligonucleotide linker containing the HIV-1 Rev NES via unique PstI and BglII restriction sites. The GFP-Ap-SV40NLS construct was made by PCR amplification of Apoptin amino acids 1-88 with simultaneous addition of SV40 LT NLS sequence (PKKKRKV (SEQ ID NO:18)) to the C-terminus followed by cloning into pEGFP-CI via engineered EcoRI/BamHI sites. To construct the dsRed fusion to the dominant negative Ran mutant (dsRed-dnRan), a construct expressing dnRan (a gift from Dr. Lan Xu, University of Massachusetts Medical School, Worcester, Mass.) was PCR amplified and cloned into pDsRed1-N1 via engineered HindIII/BamHI sites to create an in-frame fusion to the N-terminus of dsRed. All constructs were confirmed by restriction digests analysis and DNA sequencing.

Example 2

Apoptin Co-Immunoprecipitates with Subunit 1 of the Anaphase-Promoting Complex in Transformed Cells To optimize expression of Apoptin for proteomic studies, an adenovirus (Ad) expressing FLAG-tagged Apoptin (Ad-Apwt) was constructed as described in Example 1.

Saos-2, H1299, and primary foreskin fibroblast cells (PFFs) were obtained from ATCC and maintained in Dulbecco's modified Eagle's medium supplemented with 10% fetal bovine serum plus 10 µg/ml streptomycin and 10 U/ml penicillin (Sigma) at 37° C. under 5% $CO_2$ (95% air).

Apoptin protein expression was confirmed by immunoblot using an anti-FLAG monoclonal antibody. Briefly, proteins were resolved by SDS-PAGE and transferred to nitrocellulose. Blots were blocked with 5% milk in TBS-T and probed with an anti-FLAG M2 monoclonal (Sigma) antibody followed by an appropriate HRP-conjugated anti-Ig secondary antibody (Amersham Biosciences).

To generate kill curves, Ad-Apwt- and Ad-LacZ-infected H1299 and Saos-2 cells were harvested by trypsinization, washed in PBS and monitored for cell viability by trypan blue exclusion. Apoptotic assays using GFP-Apoptin deletion mutants were performed by transfecting the deletion panel into H1299 cells, and 4 days later, cells were fixed with 4% paraformaldehyde and stained with DAPI. Percent apoptosis was scored as the percent of 100 GFP positive cells showing apoptotic morphology. Results were collected in a blind study by at least three individuals in two separate experiments. Data was graphed after subtraction of GFP background; all mutant samples are shown as percent apoptosis of wild type. For Annexin V analysis, cells were stained using the Annexin V-PE Apoptosis Detection Kit-I (BD Pharmingen) and analyzed using a Guava Personal flow cytometer (Guava Technologies, Inc.). Data points were collected as percent Annexin V positive cells per 5000 events. For cell cycle analysis, cells were harvested by trypsinization, fixed and stained with propidium iodide and analyzed by FACS.

FIG. 1A shows that following infection with Ad-Apwt, p53 null Saos-2 osteosarcoma cells underwent pronounced apoptosis after 24 hours and most cells were dead by 72 hours. Little or no cell death was observed in cells infected with a control adenovirus expressing LacZ (Ad-LacZ). Similar results were obtained in H1299 cells, a p53 negative non-small cell lung carcinoma cell line.

Figure 1B:
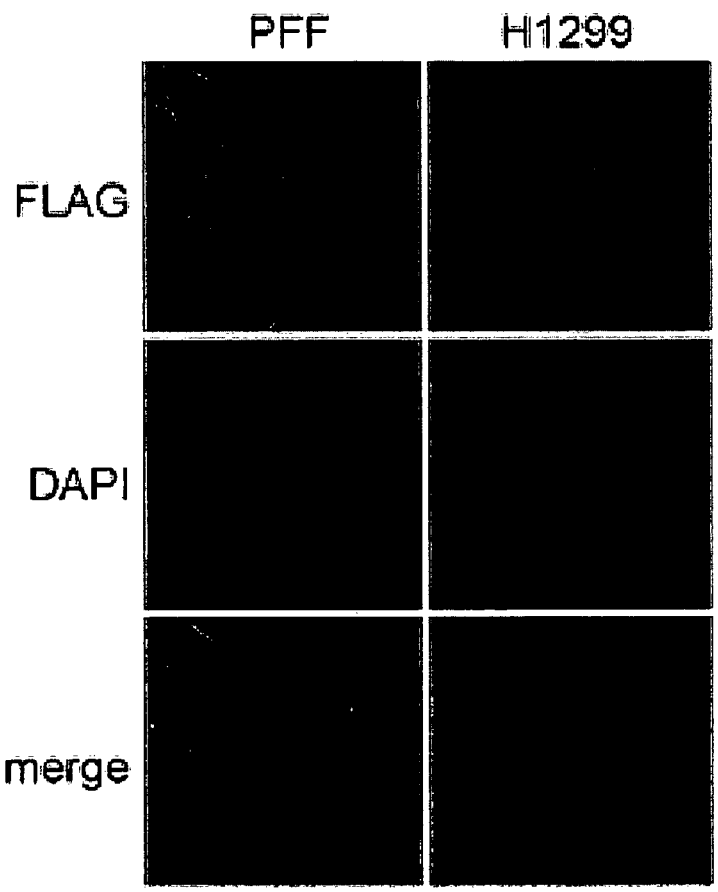
FIG. 1B is a panel of six photomicrographs showing immunofluorescence of PFF (left column) and H1299 (right column) cells, 24 hours after infection with Ad-Apwt. Cells were stained with an anti-FLAG antibody (top row) or DAPI (middle); merged images are shown in the bottom row. Magnification 1000x.

Previous studies have shown that Apoptin is localized to the nucleus in transformed cells, but is cytoplasmic in untransformed or primary cells (Danen-Van Oorschot et al., Proc. Natl. Acad. Sci., 94:5843-5847 (1997)). To determine the intracellular localization of FLAG-tagged Apoptin, immunocytochemistry was performed using an anti-FLAG monoclonal antibody. FIG. 1B shows that in primary foreskin fibroblasts (PFFs), Apoptin stained with a characteristic cytoskeletal-like pattern with nuclear exclusion, whereas in transformed H1299 cells the protein was completely nuclear.

These results suggest that the protein may be associated with cytoskeletal components. In summary, FLAG-tagged Apoptin induces apoptosis and exhibits the characteristic differential localization in transformed and primary cells described previously (Danen-Van Oorschot et al., 1997, supra).

Figure 1C:
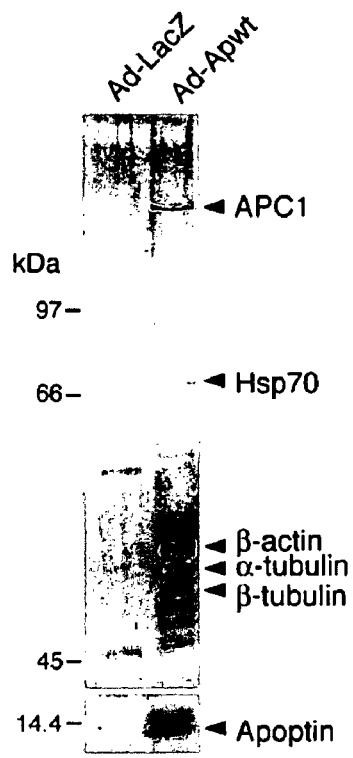
FIG. 1C is a reproduction of a gel showing the results of affinity purification of Apoptin associated proteins from H1299 cells infected with Ad-Apwt. Proteins were separated by SDS-PAGE and visualized by silver staining. Micro-sequenced bands are indicated.

To identify Apoptin-associated cellular proteins, extracts were prepared from H1299 cells infected with Ad-Apwt, and purified Apoptin and associated proteins on an anti-FLAG affinity resin. Polypeptides bound to the affinity column were separated by SDS-PAGE and visualized by silver staining. Matrix-assisted laser desorption/ionization-time of flight (MALDI-TOF) mass spectroscopic analysis revealed that a major Apoptin-associated polypeptide was APC1 (anaphase promoting complex subunit 1, also known as Cyclosome subunit 1, Protein TSG24, and Mitotic checkpoint regulator (MCPR)), the largest subunit of the APC/C (anaphase promoting complex/cyclosome), a cell cycle-regulated E3 ubiquitin ligase that controls progression through mitosis and the G1 phase of the cell cycle, an essential component of the mitotic checkpoint apparatus (FIG. 1C). Apoptin also co-immunoprecipitated with HSP-70, which is known to associate with over-expressed proteins, as well as α-tubulin, β-tubulin and β-actin, suggesting an association with filamentous networks, consistent with the immunocytochemistry results of FIG. 1B.

To confirm the association with APC1, Apoptin was immunoprecipitated from Ad-Apwt-infected H1299 cells with an anti-FLAG antibody and the immunoprecipitate analyzed for APC1 by immunoblotting. Briefly, ~8×10$^7$ cells were infected with FLAG-tagged Ad-Apwt. After 24 hours, cells were washed in PBS, harvested by scraping and lysed in Buffer X (50 mM Tris, pH 8.5, 250 mM NaCl, 1 mM EDTA, 1% NP40, Complete Mini tablet (Roche)) on ice for 20 min. Following centrifugation, lysates were pre-cleared with Protein A/G-agarose for 1 hour followed by incubation with FLAG-agarose at 4° C. for 4 hours. Beads were washed in Buffer X and eluted using FLAG-peptide. Eluates were resuspended in 1×SDS sample buffer and boiled for 5 min. Proteins were resolved by SDS-PAGE and visualized by silver staining using the SilverQuest kit (Invitrogen). Bands were excised and submitted for MALDI-TOF mass spectrometry.

For co-immunoprecipitations, ~2×10$^7$ cells were infected with Ad-Apwt or Ad-LacZ, and harvested and lysed as described above. Following centrifugation, supernatants were incubated with 20 μl equilibrated EZview Red anti-FLAG M2 affinity beads (Sigma) at 4° C. for 4 hours. Beads were washed in Buffer X and bound proteins were eluted in 1×SDS sample buffer by boiling for 5 min.

Figure 1D:
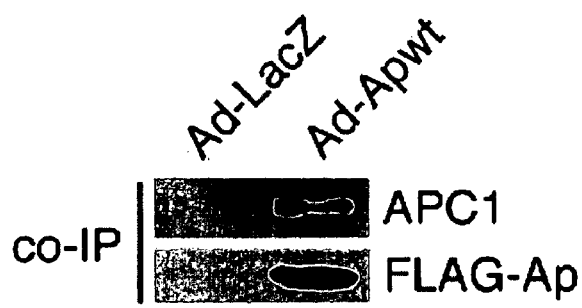
FIG. 1D is a reproduction of two immunoblots showing Apoptin immunoprecipitated from Ad-Apwt- (right lane) and Ad-LacZ- (left lane) infected H1299 cells using an anti-FLAG antibody (bottom panel), and the immunoprecipitates were analyzed for APC1 by immunoblotting with a polyclonal anti-APC1 antibody (top panel).
Figure 1E:
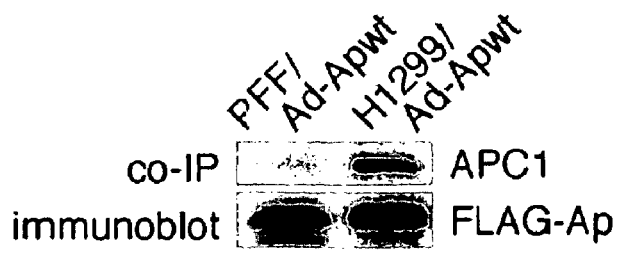
FIG. 1E is a reproduction of two immunoblots showing Apoptin immunoprecipitated from Ad-Apwt-infected PFF (left lane) or H1299 (right lane) cells using an anti-FLAG antibody (bottom panel), and the immunoprecipitates were analyzed for APC1 by immunoblotting (top panel). Immunoblotting for FLAG-Apoptin was performed on whole cell extracts.

FIG. 1D shows that APC1 was present in the immunoprecipitate from Apoptin but not in that of a control LacZ protein. By contrast, FIG. 1E shows that APC1 did not co-immunoprecipitate with Apoptin in PFFs, suggesting that the Apoptin-APC1 association is specific to transformed cells.

Example 3

Apoptin Expression in Transformed Cells Induces G2/M Cell-Cycle Arrest by Inhibition of APC/C Function The association of Apoptin with APC1 raised the possibility that Apoptin expression could affect cell-cycle progression. To address this issue, H1299 and PFF cells were infected with Ad-Apwt or Ad-LacZ and analyzed by fluorescence activated cell sorting (FACS).

Figure 2A:
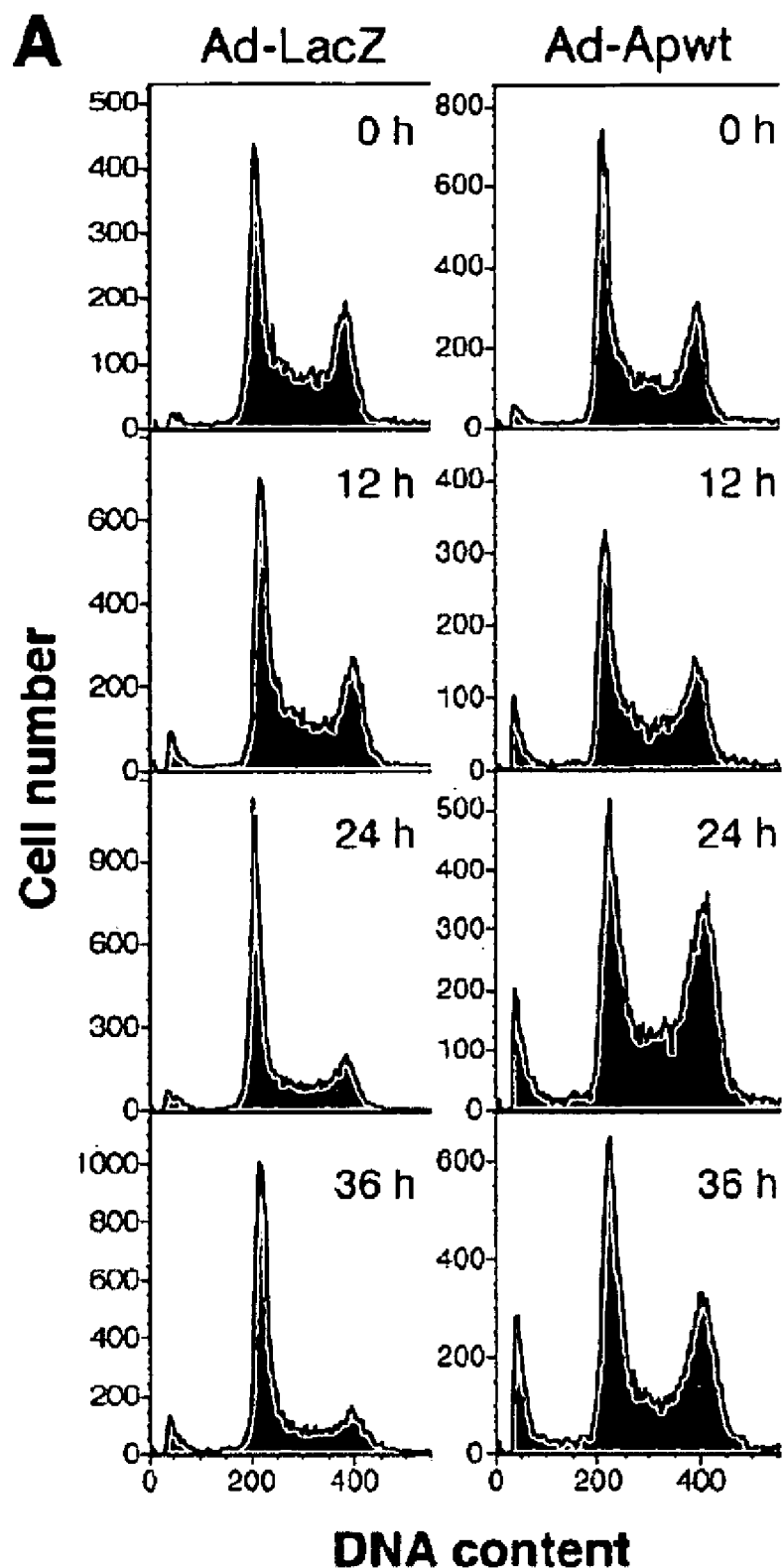
FIG. 2A is a series of histograms showing the results of cell cycle analysis of H1299 cells infected with either Ad-LacZ (left column) or Ad-Apwt (right column) at 0, 12, 24 and 36 hours (h) post-infection, as indicated.
Figure 2B:
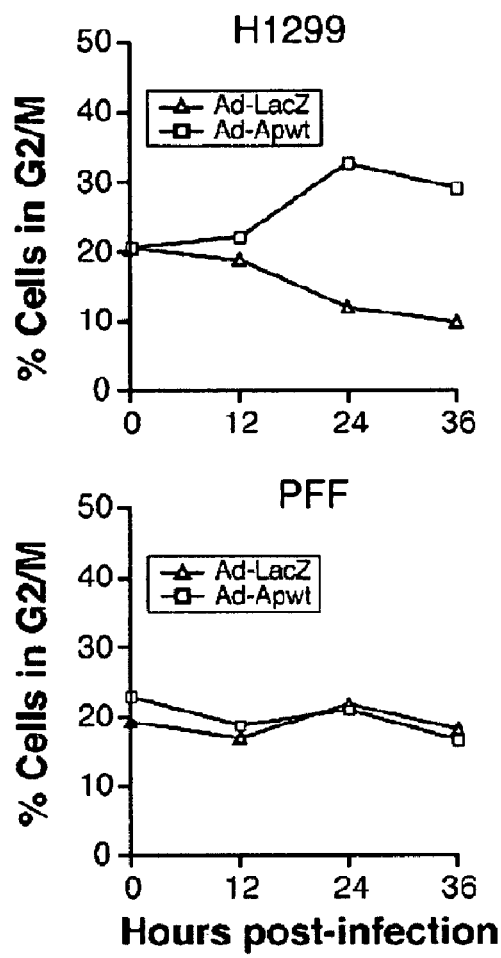
FIG. 2B is a pair of line graphs showing the percent of H1299 (top) or PFF (bottom) cells in G2/M at 0, 12, 24, or 36 hours post transfection.
Figures 5A, 5B, 5C:
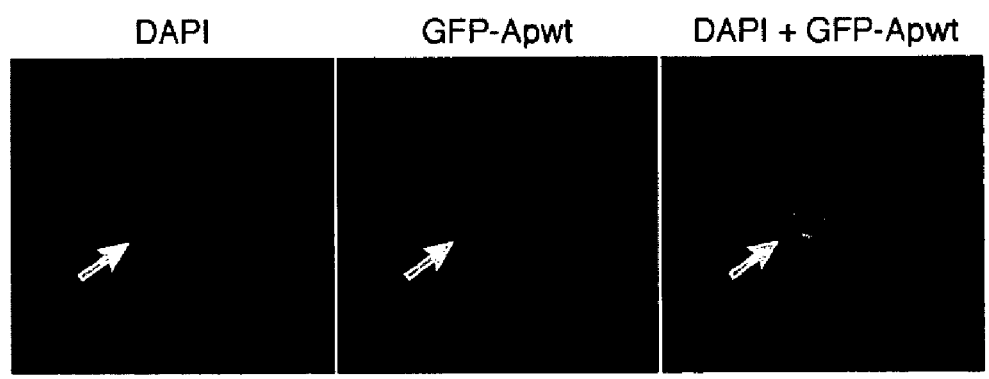
FIGS. 5A-C are a series of three photomicrographs demonstrating that Apoptin expression in transformed cells results in a condensed nuclear morphology. Immunofluorescence of H1299 cells 4 days post-transfection with GFP-Apwt. Cells were fixed with 4% paraformaldehyde and stained with DAPI (5A); or visualized for GFP staining (5B); merged images are shown in FIG. 5C. Magnification 1000×.

FIGS. 2A and B show that following infection with Ad-Apwt, H1299 cells began to accumulate in G2/M after 12 hours whereas the cell-cycle profile of PFF cells was unaffected. Although FACS analysis of Apoptin-expressing H1299 cells clearly showed a 4N DNA content, morphological examination did not reveal a classical mitotic-arrested appearance but rather a condensed nuclear morphology that is a hallmark of apoptosis (FIG. 5). The onset of apoptosis was rapid, as evidenced by the appearance of a prominent sub-G1 peak concomitant with G2/M accumulation.

To verify that Apoptin inhibited APC/C function in H1299 cells, an independent assay was used to measure APC/C activity. The APC/C catalyzes the ubiquitination of several substrates including cyclin B1 and Polo-like kinase (Plk), whose degradation by the proteasome results in anaphase progression and mitotic exit. If APC/C function is inhibited, these substrates are not degraded. Thus, stabilization of APC/C substrates is indicative of cyclosome dysfunction (Wirth et al., Genes & Dev., 18:88-98 (2004)). To test whether Apoptin expression resulted in stabilization of APC/C substrates, H1299 cells were infected with Ad-Apwt or Ad-LacZ, and 24 hours later levels of mitotic APC/C substrates were determined by immunoblotting. As a positive control, cells were arrested in G2/M by nocodazole treatment.

Proteins were resolved by SDS-PAGE and transferred to nitrocellulose. Blots were blocked with 5% milk in TBS-T and probed with either anti-FLAG M2 monoclonal (Sigma), anti-APC1 polyclonal (affinity purified anti-peptide serum), anti-Cdc27 monoclonal (Santa Cruz); anti-cyclin B1 (Upstate Biotech); anti-Plk (Zymed Laboratories, Inc.), anti-cyclin E (Upstate Biotech) or anti-tubulin (Sigma) antibodies followed by appropriate HRP-conjugated anti-Ig secondary antibody (Amersham Biosciences).

Figure 2C:
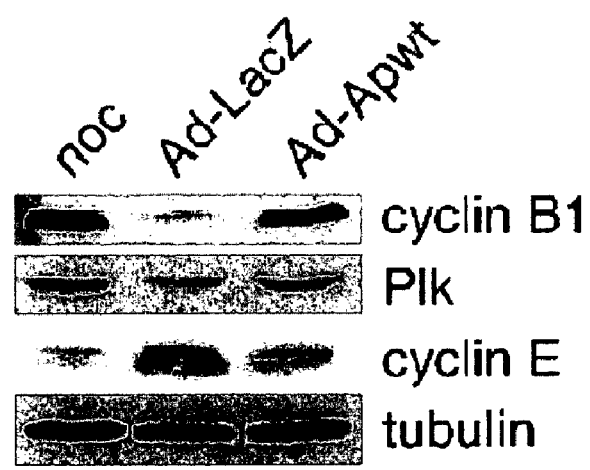
FIG. 2C is a set of four immunoblots showing the results of analysis of APC/C (anaphase promoting complex/cyclosome) substrates cyclin B1 (top row) and Polo-like kinase (Plk, second row), and a non-APC/C substrate, cyclin E (third row), in H1299 whole-cell lysates 24 hours following infection with Ad-Apwt (right lane) or Ad-LacZ (center lane), or in cells treated with nocodozole (noc; left lane) for 12 hours. Tubulin levels (bottom row) were monitored as a loading control.

FIG. 2C shows that the protein levels of cyclin B1 and Plk were stabilized in Ad-Apwt-infected and nocodozole-treated cells compared to Ad-LacZ-infected cells. By contrast, protein levels of cyclin E, a G1 cyclin that is not an APC/C substrate, were slightly decreased by Apoptin expression or nocodazole treatment.

RT-PCR was performed to confirm that Apoptin did not affect cyclin B1 or Plk mRNA levels. RT-PCR was carried out using the following primer pairs:

```
cyc B 1:
5' TACTGCCTCTCCAAGCCCAATG      (SEQ ID NO:9)
and
3' AGATGCTCTCCGAAGGAAGTGC;     (SEQ ID NO:10)

Plk:
5' ATTCCCAAGCACATCAACCCCGTG    (SEQ ID NO:11)
and
3' CAGGCTGTCACCATCATTGTAGAG;   (SEQ ID NO:12)

GAPDH:
5' ACCACAGTCCATGCCATCAC        (SEQ ID NO:13)
and
3' TCCACCACCCTGTTGCTGTA.       (SEQ ID NO:14)
```

PCR Reaction conditions were as follows: 1 cycle of 95° C. for 2 minutes; 25 cycles of 94° C. (denaturation) for 15 seconds, 65° C. (annealing) for 30 seconds, and 72° C. (extension) for 1 minute; 1 cycle of 72° C. for 7 minutes (final extension).

RT-PCR analysis confirmed that Apoptin did not affect cyclin B1 or Plk mRNA levels (FIG. 6). These results indicate that Apoptin inhibits cyclosome function leading to G2/M arrest and apoptosis.

To gain insight into how Apoptin might inhibit APC/C activity, gel filtration analysis was performed of the APC/C complex in mock- or Ad-Apwt-infected H1299 cells. Fractions from the gel filtration column were analyzed by immunoblotting for APC1 or another APC/C subunit, Cdc27 (APC3). Briefly, H1299 cells (~2×10$^7$) were either mock- or Ad-Apwt-infected and after 24 hours, cells were washed in PBS, harvested by scraping and lysed in Buffer A (20 mM Tris, pH 7.5, 100 mM NaCl, 20 mM b-glycerophosphate, 0.2% NP-40, 10% glycerol, 0.5 mM DTT, Complete Mini Tablet (Roche)) on ice for 30 min. Lysates were sonicated for 10 sec, centrifuged for 1 hour at 100,000 g, and ~500 μg of total protein was injected into a Pharmacia FPLC apparatus and separated on a Superose 6 10/30 (Pharmacia) column. Fractions (500 μl) were collected and precipitated with 20% Trichloroacetic acid (TCA) on ice for 1 hour. Precipitates were then centrifuged at 13,000 g for 15 min, washed with −20° C. acetone, dried, resuspended in 1×SDS sample buffer and boiled for 5 min.

Figure 2D:
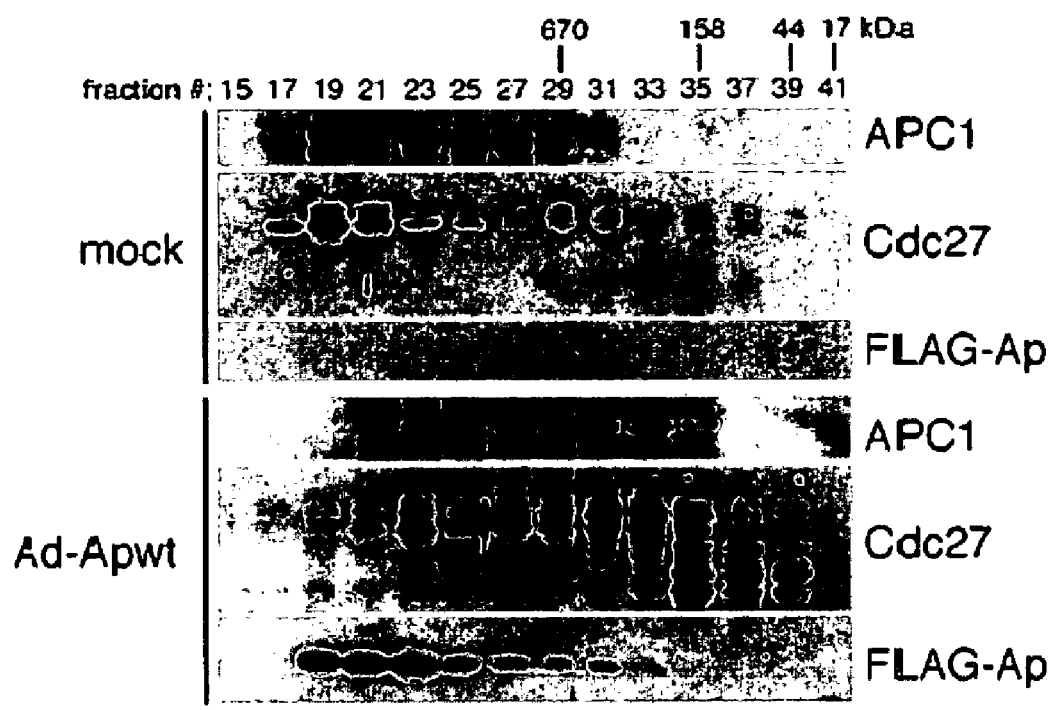
FIG. 2D is a reproduction of the results of gel filtration analysis of the APC/C complex in mock- or Ad-Apwt-infected H1299 cells, as indicated. Fractions from the gel filtration column were analyzed by immunoblotting for FLAG-Apoptin, APC1 or another APC/C subunit, Cdc27. Positions of molecular weight markers are indicated.

The results, shown in FIG. 2D, reveal two dramatic effects of Apoptin expression on the APC/C complex. First, following Apoptin expression, both APC1 and Cdc27 migrated at significantly lower native molecular weights, strongly suggesting disruption of the APC/C complex. In fact, in Apoptin-expressing cells some APC1 migrated at the size expected for a free subunit (~200 kDa). Second, in Apoptin-expressing cells Cdc27 degradation products appeared in the lower molecular weight range. Collectively, these results suggest a model in which Apoptin binds to APC1, leading to disruption of the APC/C complex and the resultant degradation of some APC/C subunits. Despite its small size (13.6 kDa), essentially all Apoptin migrated at a native molecular weight range of from about 200 kDa to greater than 1 Mda, consistent with the possibility that Apoptin is associated with one or more large multi-subunit complexes.

Example 4

Figure 3A:
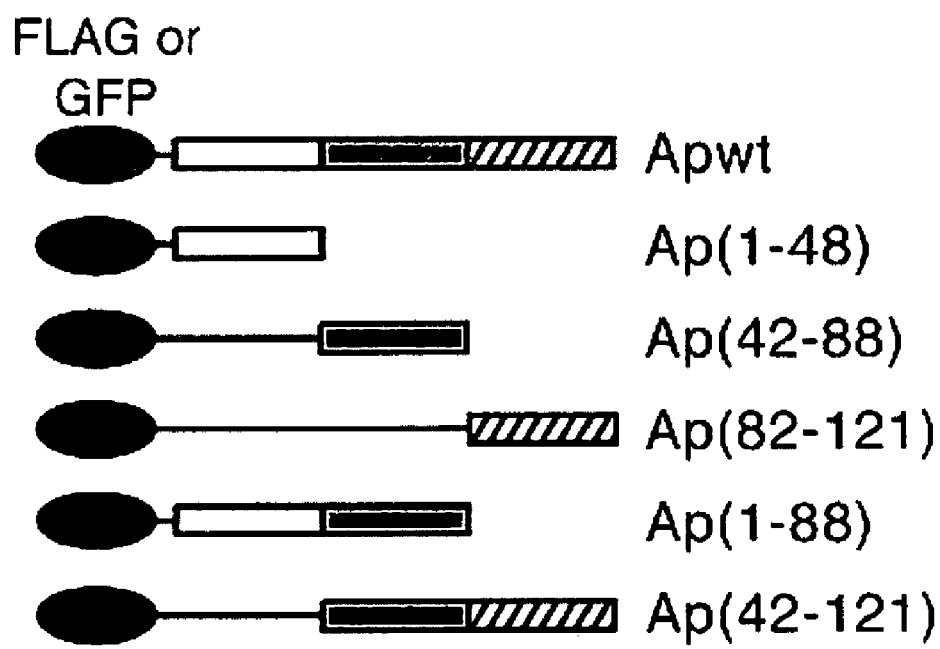
FIG. 3A is a schematic representation of N-terminal FLAG- or GFP-tagged Apoptin deletion mutants.

The C-terminal Domain of Apoptin is Required for Association with APC1 and Apoptosis To delineate the region of Apoptin required for association with APC1, a panel of FLAG-tagged Apoptin deletion mutants (FIG. 3A) was transiently expressed in H1299 cells. ~1×10$^7$ cells were transiently transfected with 3XFLAG-Apoptin truncation mutants using Effectene reagent (Qiagen). Forty-eight hours following transfection, Apoptin was immunoprecipitated with an anti-FLAG antibody, and the immunoprecipitate analyzed for APC1 by immunoblotting as described for the co-immunoprecipitation experiments.

Figure 3B:
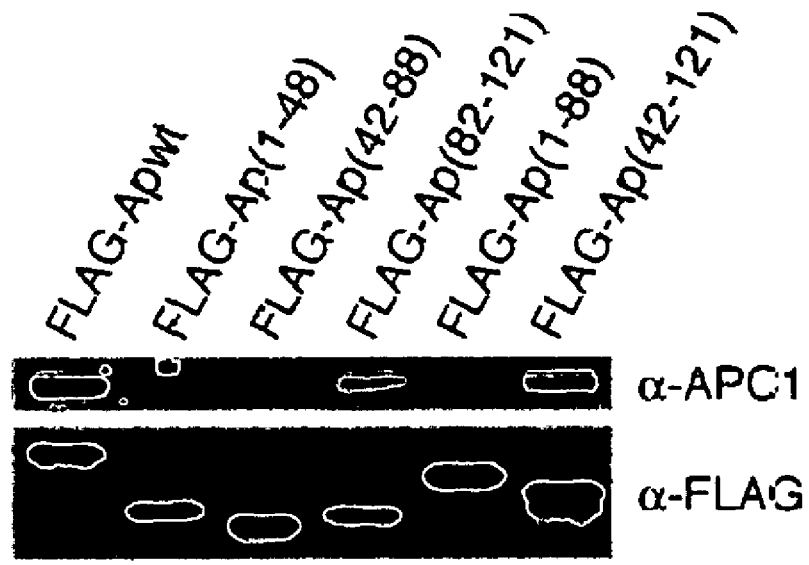
FIG. 3B is a pair of immunoblots of H1299 cells transfected with FLAG-Apoptin deletion constructs. 48 hours later, Apoptin was immunoprecipitated with an anti-FLAG antibody and the immunoprecipitate was analyzed for APC1 (top blot) and Apoptin (bottom blot) by immunoblotting.

FIG. 3B shows that APC1 was present only in immunoprecipitates of Apoptin derivatives that contained the C-terminal domain (amino acids 82-121; SEQ ID NO:17).

To determine whether association with APC1 is required for Apoptin-mediated cell death, green fluorescent protein (GFP)-tagged derivatives of the Apoptin deletion mutants were transiently expressed in H1299 cells. Four days follow-ing transfection, cells were fixed, stained with DAPI and analyzed by fluorescence microscopy for apoptotic morphology. Briefly, PFF and H1299 cells were infected with Ad-Apwt, and 24 hours later, cells were fixed in 4% paraformaldehyde (in PBS), permeablized in 0.5% TritonX-100 (in PBS) and stained with anti-FLAG M5 monoclonal antibody (Sigma) followed by anti-mouse Ig Texas Red conjugated secondary antibody (Jackson Laboratories). Cells were visualized with a Zeiss Axiophot2 fluorescence microscope using Axiovision 3.1 software.

Figure 3C:
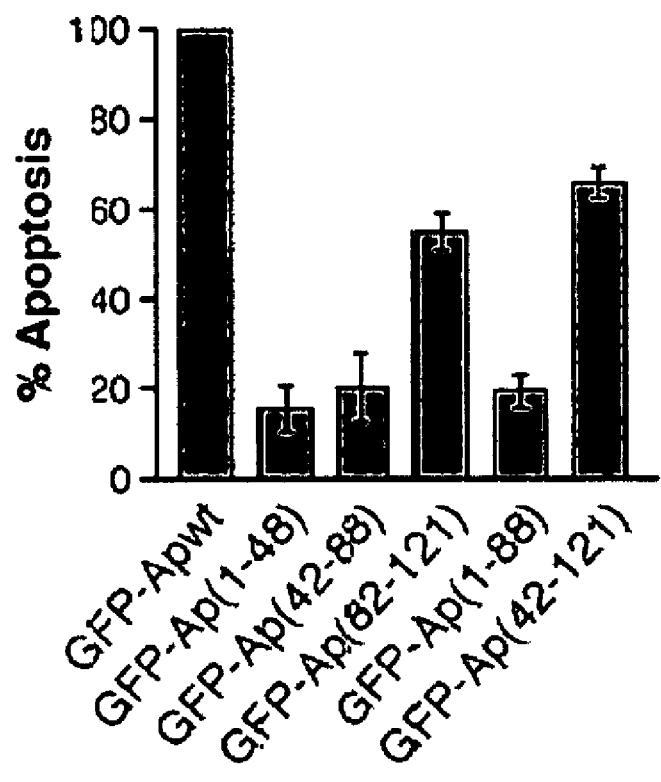
FIG. 3C is a bar graph showing percent apoptosis in H1299 cells transfected with a number of GFP-Apoptin deletion constructs. Four days later, the cells were fixed and stained with DAPI and analyzed by fluorescence microscopy for GFP expression associated with apoptotic morphology. The percent apoptosis in cells expressing GFP alone was taken as background and subtracted from all samples. All mutant samples are shown as percent apoptosis of Apwt.

FIG. 3C shows that the ability of mutants lacking the C-terminal domain to induce cell death was significantly reduced. By contrast, Apoptin mutants Ap(82-121) (SEQ ID NO:17) and Ap(42-121) (SEQ ID NO:16) retained 55 and 67 percent of wild-type killing activity, respectively. Collectively, the results of FIGS. 3B and C indicate that the C-terminal domain of Apoptin is necessary and sufficient for induction of apoptosis, and suggest that association with APC1 is responsible for G2/M arrest and cell death.

Example 5

Loss of APC1 Induces G2/M Arrest and Apoptosis in the Absence of p53

The results described above suggest a model whereby Apoptin inhibits APC/C function resulting in G2/M arrest followed by apoptosis. A prediction of this model is that inhibition of APC1 through other means should have an effect similar to that of Apoptin expression.

To test this prediction, APC1 was deleted by RNA interference (RNAi) in H1299 cells. Double-stranded RNAs (ds-RNAs) were synthesized in vitro using a 500 bp PCR fragment as the template. Primer sequences, containing T7 priming sites, were as follows:

```
APC1:
5'-GCGTAATACGACTCACTATAGGGAGAAAAGGAGT    (SEQ ID NO:3)
AAGTGAAATTGG-3'
and

5'-GCGTAATACGACTCACTATAGGGAGAGGAAAGGT    (SEQ ID NO:4)
GAAGTCACAGGG-3'

Lamin A/C:
5'-GCGTAATACGACTCACTATAGGGAGAGGCAGTCT    (SEQ ID NO:5)
GCTGAGAGGAAC- 3'
and

5'-GCGTAATACGACTCACTATAGGGAGAAGGTGTTC    (SEQ ID NO:6)
TGTGCCTTCCAC- 3'
```

This produced full-length PCR products as follows:

```
APC1:
                                                              (SEQ ID NO:7)
      2392                                                    aaattggggg
      2401 ccttatgtag atcattacta tagagactac ccaacgcttg tcagaactac tggacaagtg
      2461 tgcacaattg atccaggtca aacaggattt atgcatcatc catcattttt tacgtctgag
      2521 ccaccaagta tttatcagtg ggtgagttct tgtctgaagg gtgaaggaat gccaccttat
      2581 ccttacctcc ctggaatctg tgaaagaagc agacttgtag tcttgagtat tgcactgtac
      2641 atacttggtg atgagagctt ggtttctgat gaatcctcac agtatttaac cagaataact
      2701 atagcccccc agaagttgca agtagaacaa gaggaaaaca ggtttagttt caggcattct
      2761 acatctgttt ctagtctagc tgaaagattg gttgtctgga tgactaatgt aggattcact
      2821 ttaagagatt tggaaactct tccctttgga attgctcttc ccatcagaga tgcaatttat
      2881 cactgtcgtg agcagcctgc ctcagactgg ccagaagctg tctgtctctt gattggacgt
      2941 caggatcttt ccaagcaggc ctgcgaagga aacttaccca aagggaagtc tgtgctctca
```

-continued
```
3001 tcagatgttc cttcaggaac agaaactgag gaggaagatg acggcatgaa tgacatgaat
3061 cacgaggtca tgtcattaat atggagtgaa gatttaaggg tgcaggatgt gcgaaggctt
3121 cttcagagtg cgcatcctgt ccgtgtcaac gtagtgcagt acccagagct cagtgaccac
3181 gagttcatcg aggaaaagga aaacagattg ctccaattgt gtcagcgaac tatggctctt
3241 cctgtaggac gaggaatgtt taccttgttt tcgtaccatc ctgttccaac agagccattg
3301 cctattccta aattgaatct gactgggcgt gccccctcctc ggaacacaac agtagacctt
3361 aatagtggaa acatcgatgt gcctcccaac atgacaagct gggccagctt tcataatggt
3421 gtggctgctg gcctgaagat agctcctgcc tcccagatcg actcagcttg gattgtttac
3481 aataagccca agcatgctga gttggccaat gagtatgctg gctttctcat ggctctgggt
3541 ttgaatgggc accttaccaa gctggcgact ctcaatatcc atgactactt gaccaagggc
3601 catgaaatga caagcattgg actgctactt ggtgtttctg ctgcaaaact aggcaccatg
3661 gatatgtcta ttactcggct tcttagcatt cacattcctg ctctcttacc cccaacgtcc
3721 acagagctgg atgttcctca caatgtccaa gtggctgcag tggttggcat tggccttgta
3781 tatcaaggga cagctcacag acatactgca gaagtcctgt tggctgagat aggacggcct
3841 cctggtcctg aaatggaata ctgcactgac agagagtcat actccttagc tgctggcttg
3901 gccctg
```

Lamin A/C:
(SEQ ID NO:8)
```
 784    gaggaac tggacttcca gaagaacatc tacagtgagg agctgcgtga gaccaagcgc
 841 cgtcatgaga cccgactggt ggagattgac aatgggaagc agcgtgagtt tgagagccgg
 901 ctggcggatg cgctgcagga actgcgggcc cagcatgcgg accaggtgga gcagtataag
 961 aaggagctgg agaagactta ttctgccaag ctggacaatg ccaggcagtc tgctgagagg
1021 aacagcaacc tggtgggggc tgcccacgag gagctgcagc agtcgcgcat ccgcatcgac
1081 agcctctctg cccagctcag ccagctccag aagcagctgg cagccaagga ggcgaagctt
1141 cgagacctgg aggactcact gcccgtgag cgggacacca gccggcggct gctggcggaa
1201 aaggagcggg agatggccga gatgcgggca aggatgcagc agcagctgga cgagtaccag
1261 gagcttctgg acatcaagct ggccctggac atggagatcc acgcctaccg caagctcttg
1321 gagggcgagg aggagaggct acgcctgtcc cccagcccta cctcgcagcg cagccgtggc
1381 cgtgcttcct ctcactcatc ccagacacag ggtggggggca gcgtcaccaa aaagcgcaaa
1441 ctggagtcca ctgagagccg cagcagcttc tcacagcacg cacgcactag cgggcgcgtg
1501 gccgtggagg aggtggatga ggagggcaag tttgtccggc tgcgcaacaa gtccaatgag
1561 gaccagtcca tgggcaattg gcagatcaag cgccagaatg gagatgatcc cttgctgact
1621 taccggttcc caccaaagtt caccctgaag gctgggcagg tggtgacgat ctgggctgca
1681 ggagctgggg ccacccacag ccccccctacc gacctggtgt ggaaggcaca gaacacctgg
1741 ggctgcggga acagcctgcg tacggctctc atcaactcca ctggggaaga agtggccatg
1801 cgcaagctgg tgcgctcagt gactgtggtt gaggacgacg aggatgagga
```

In vitro transcription was performed using the T7 Megascript Kit (Ambion), and the ds-RNA products were cleaved using the Dicer siRNA Generation Kit (Gene Therapy Systems, Inc.) to generate diced siRNAs of unknown sequence. The pool of diced siRNAs was then transfected into cells using Oligofectamine (Invitrogen) as described previously (Elbashir et al., Nature, 411:494-498 (2001)).

Caspase-3 activation assays were also performed. Briefly, H1299 cells were transfected using Oligofectamine (Invitrogen) with siRNAs directed against Lamin A/C or APC1; 48 hours later, whole cell extracts were made by lysing cells in SDS sample buffer. Cell extracts were analyzed by SDS-PAGE and immunoblotted with a monoclonal antibody against human caspase-3 (H-277, Santa Cruz).

For cell viability assays, H1299 and PFF cells infected with Ad-Apwt, Ad-pmNES or Ad-LacZ were harvested by trypsinization, washed in PBS and stained with ViaCount reagent (Guava Technologies, Inc., Burlingame, Calif.), and viability was quantitated using a Guava Personal flow cytometer. Data points were collected as percent cell viability per 5000 events. Apoptosis assays were performed with GFP-Apoptin fusion proteins as described herein.

Figure 4A:
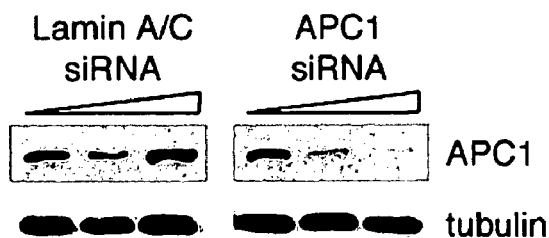
FIG. 4A shows four immunoblots of H1299 cells transfected with 0, 0.05 and 0.5 μg siRNAs directed against either Lamin A/C (left column) or APC1 (right column); APC1 expression was detected using an anti-APC1 antibody (top row). Tubulin was monitored as a loading control (bottom row).

FIG. 4A demonstrates that transfection of a pool of small interfering RNAs (siRNAs) directed against APC1 resulted in specific and near complete reduction of APC1 protein levels. By contrast, a comparable pool of siRNAs directed against the control Lamin A/C had no significant effect on APC1 levels.

Figure 4B:
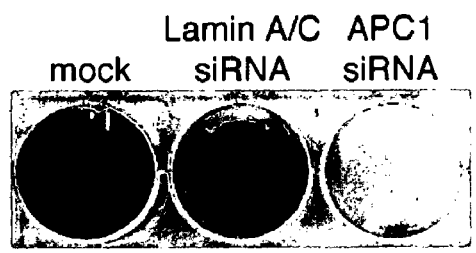
FIG. 4B is a photograph of crystal violet staining of H1299 cells following two rounds of transfection with Lamin A/C or APC1 siRNAs, or mock-transfected.
Figure 4C:
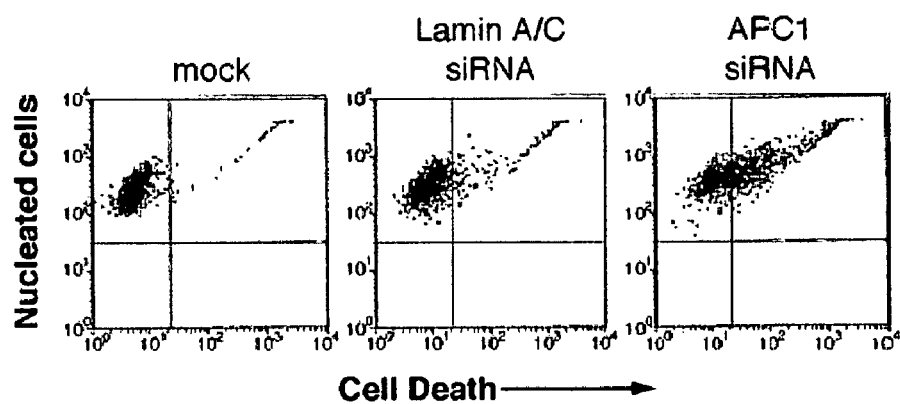
FIG. 4C is a set of three scatter graphs showing cell viability assays of H1299 cells 48 hours following transfection of Lamin or APC1 siRNAs, or mock-transfected.
Figure 4D:
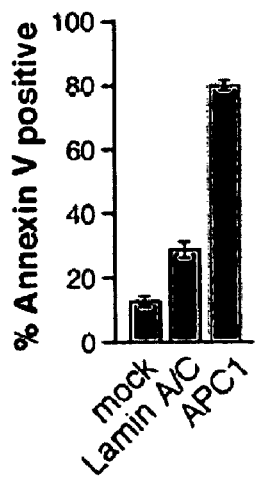
FIG. 4D is a bar graph showing the percent of annexin V-FITC staining to monitor apoptosis in Lamin A/C or APC1 siRNA-transfected cells.
Figure 4E:
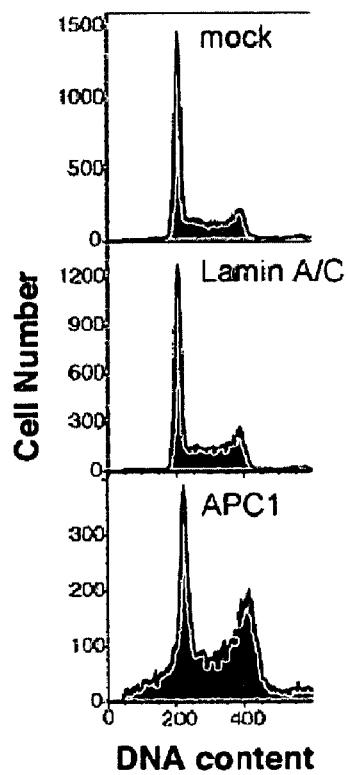
FIG. 4E is a panel of three histograms showing the results of cell cycle analysis of Lamin A/C or APC1 siRNA-transfected or mock-transfected cells.
Figure 4F:
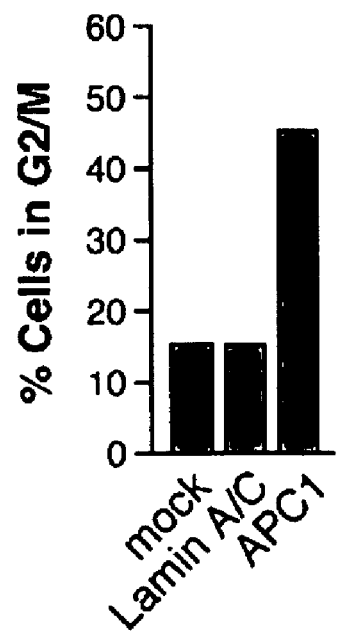
FIG. 4F is a histogram showing the results of quantitation of the percentage of cells arrested in G2/M of Lamin A/C or APC1 siRNA-transfected or mock-transfected cells.

Transfection of the APC1 siRNA pool resulted in a dramatic reduction in cell density (FIG. 4B) and viability (FIG. 4C) compared to the Lamin A/C siRNA- and mock-transfected controls. Annexin V-FITC staining (FIG. 4D) and caspase-3 activation (FIG. 7) confirmed, as expected, that cell death in APC1 siRNA-transfected cells was due to apoptosis, analogous to that observed following Apoptin expression (Danen-van Oorschot et al., J. Virol., 74:7072-7078 (2000)). FIG. 4E shows that transfection of APC1 siRNAs, but not the control Lamin A/C siRNAs, resulted in G2/M accumulation and the appearance of cells in the sub-G1 region. Quantitation of the FACS data indicates that nearly 50% of APC1 siRNA-transfected cells were arrested in G2/M compared to approximately 15% for the Lamin A/C siRNA- or mock-transfected controls (FIG. 4E).

Thus, RNAi-mediated depletion of APC1 has an effect analogous to that observed following Apoptin expression, resulting in accumulation of cells in G2/M and the appearance of cells in the sub-G1 region. Thus, RNAi-mediated depletion of APC1 can be used to induce G2/M arrest and apoptosis.

Example 6

Translocation of Apoptin in Primary Cells

The ability of the chicken anemia virus protein Apoptin to localize to either the nucleus or cytoplasm depending on cell type suggested the protein may undergo nucleo-cytoplasmic shuttling. To determine whether Apoptin shuttles in primary cells, about $5 \times 10^5$ primary foreskin fibroblasts (PFF; ATCC #CRL-2056) were transiently transfected using an Amaxa Nucleofector with a plasmid expressing Apoptin fused to the C-terminus of green fluorescent protein (GFP-Apwt), and 24 hours later were treated with leptomycin B (LMB) at a final concentration 2.5 ng ml-1. LMB is a compound that specifically blocks Crm1-mediated nuclear export (Wolff et al., Chem. Biol. 4, 139-147 (1997); Kudo et al., Exp. Cell Res. 242, 540-547 (1998)).

PFF cells were maintained in Dulbecco's modified Eagle's medium (DMEM) supplemented with 10% fetal bovine serum plus 10 μg ml$^{-1}$ streptomycin and 10 U ml$^{-1}$ penicillin (Sigma, St Louis, Mo.) at 37° C. under 5% $CO_2$ (95% air). After 24 hours, the cells were fixed in 4% paraformaldehyde and stained with DAPI. Cells were mounted on slides and observed using a Ziess Axiophot2™ fluorescence microscope using Axiovision™ 4.2 software.

If Apoptin shuttles in primary cells, then blocking nuclear export should result in the accumulation of Apoptin in the nucleus. The results showed that LMB treatment resulted in nuclear accumulation of GFP-Apwt in PFFs, indicating that Apoptin shuttles in primary cells, thus, blocking Apoptin shuttling may be useful in affecting apoptosis.

Example 7

Translocation of Apoptin in Transformed Cells

To test whether Apoptin also shuttles in transformed cells, an assay was developed to monitor nucleo-cytoplasmic shuttling of a predominantly nuclear protein. A dominant-negative Ran GTPase mutant (dnRan), which blocks Ran-dependent nuclear import (Klebe et al., Biochemistry 34:639-647 (1995)) was expressed in non-small cell lung carcinoma H1299 cells. ~5×10$^5$ H1299 cells were transfected with GFP-Apwt or Rev-GFP, and 12 hours later transfected with a construct expressing dsRed-dnRan. H1299 cells were transiently transfected using Effectene reagent (Qiagen, Valencia, Calif.) and after 24 hours the cells were fixed in 4% paraformaldehyde and stained with DAPI. Cells were mounted on slides and observed using a Ziess Axiophot2™ fluorescence microscope using Axiovision™ 4.2 software.

To validate this approach, we performed a control experiment monitoring the effect of dnRan on localization of HIV Rev, a well-characterized nucleo-cytoplasmic shuttling protein (Kalland et al., Mol. Cell. Biol. 14:7436-7444 (1994); Meyer and Malim, Genes Dev., 8:1538-1547 (1994)). As expected, a dsRed-dnRan fusion-protein localized to the nuclear periphery (Gorlich et al., EMBO J. 15, 5584-5594 (1996)), and a Rev-GFP fusion-protein accumulated in the nucleolus (Venkatesh and Chinnadurai, Virology, 178:327-330 (1990)). Co-expression of dsRed-dnRan and Rev-GFP resulted in loss of nuclear GFP signal, confirming that Rev-GFP exited the nucleus and was blocked for subsequent re-entry.

Similarly, expression of dsRed-dnRan resulted in loss of nuclear GFP-Apwt, indicating that Apoptin shuttled in transformed cells. Collectively, the data indicate that Apoptin localization is regulated by nucleo-cytoplasmic shuttling in both primary and transformed cells, and that nuclear import and export are mediated by the normal cellular machinery. Thus, Apoptin shuttling can occur in both primary and transformed cells.

Example 8

Transformed Cells Contain a Dominant Activity that Confers Apoptin Nuclear Localization To determine whether transformed or primary cells contained a dominant Apoptin localization activity, a heterokaryon experiment was performed.

Briefly, about ~5×10$^5$ H1299 or PFF cells were transiently transfected with dsRed-Apwt or GFP-Apwt, respectively, by Amaxa nucleofection. Immediately following transfection, cells were either mixed or plated separately (for controls) in 6 well format on cover slips and left to recover for 12 hours. After recovery, media was removed, cells were washed twice in PBS and fused by exposure to a solution of 50% polyethylene glycol (PEG 1000) in serum-free DMEM for 125 seconds at room temperature. PEG solution was then removed by washing with PBS and fresh medium was added. After overnight recovery, cells were fixed in 4% paraformaldehyde (in PBS), stained with DAPI and Apoptin localization was determined by fluorescence microscopy as described above.

The results showed that when either PFF/GFP-Apwt or H1299/dsRed-Apwt cells were self-fused, the expected localization patterns were observed. However, fusion of PFF/GFP-Apwt cells with H1299/dsRed-Apwt cells resulted in the translocation of PFF-derived GFP-Apwt to the nucleus where it co-localized with dsRed-Apwt. These results indicate that transformed cells contain a dominant activity that confers Apoptin nuclear localization.

Localization of Apoptin was also monitored in HA1-IM (a gift from S. Bacchetti, McMaster University, Hamilton, Canada) cells, a clonal population of human embryonic kidney cells transformed with SV40 large T antigen that bypass senescence and enter crisis (Counter et al., EMBO J. 11, 1921-1929 (1992)). HA-1 cells were infected with an adenovirus expressing FLAG-tagged Apoptin (Ad-Apwt) and maintained in Dulbecco's modified Eagle's medium (DMEM) supplemented with 10% fetal bovine serum plus 10 μg ml$^{-1}$ streptomycin and 10 U ml$^{-1}$ penicillin (Sigma, St Louis, Mo.) at 37° C. under 5% $CO_2$ (95% air). Apoptin localization was monitored both before (passage 44) and after (passage 94) crisis. Apoptin exhibited a filamentous, cytoskeletal-like cytoplasmic staining pattern in pre-crisis cells, whereas in post-crisis cells Apoptin localized predominantly to the nucleus.

Thus, the dominant activity in transformed cells that directs Apoptin to the nucleus appears early during the transformation process.

Example 9

Sequence Elements that Contribute to Nucleo-Cytoplasmic Shuttling

Figure 10:
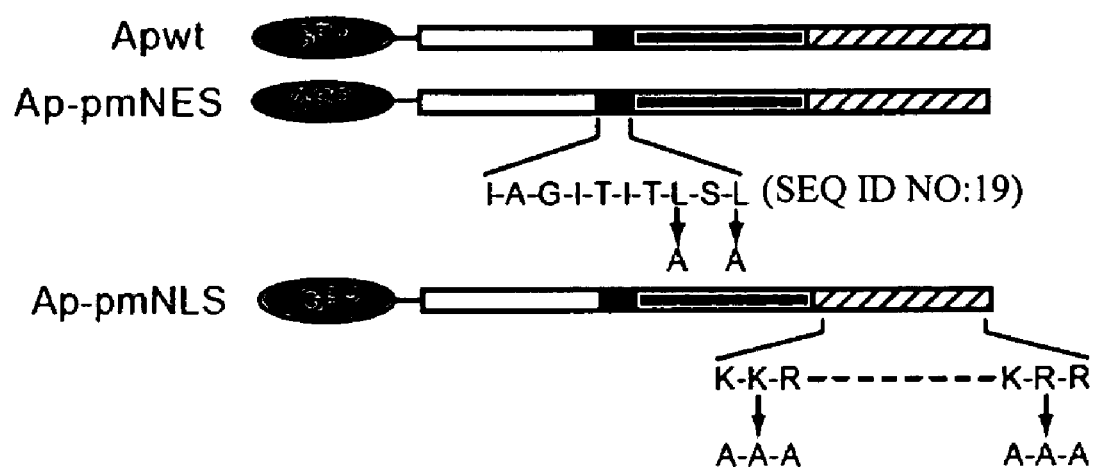
FIG. 10 is a schematic illustration of N-terminal GFP-tagged Apoptin NES and NLS mutants, showing the sequences of the core NES region (IAGITITLSL; SEQ ID NO:19), and the KKR and JRR regions of the NLS.

This Example describes experiments performed to identify the specific sequence elements that contribute to nucleo-cytoplasmic shuttling. Previous studies have noted a putative N-terminal nuclear export signal (NES) comprising amino acids 37-46 in the N-terminus and a putative C-terminal nuclear localization signal (NLS) comprising residues 70-121 in the C-terminus (shown in FIG. 10) (Danen-Van Oorschot et al., J. Biol. Chem. 278, 27729-27736 (2003); Wadia et al., J. Virol. 78, 6077-6078 (2004)). To determine whether the putative N-terminal sequence was a functional NES, a mutant in which the core residues leucine-44 and leucine-46 were mutated to alanine (GFP-Ap-pmNES) was constructed (FIG. 10).

In PFFs, GFP-Ap-pmNES mislocalized to the nucleus, indicating that the putative Apoptin ES is functional and that NES-dependent transport of Apoptin is required for cytoplasmic accumulation in primary cells. The putative bipartite NLS contains two domains highly enriched in lysine and arginine (residues 86-88 and 116-118). We constructed an NLS mutant in which both trios of basic amino acids were mutated to alanine (Ap-pmNLS). This mutant mislocalized to the cytoplasm in H1299 cells, indicating the NLS is required for nuclear localization. Thus, Apoptin contains both a functional NES and NLS, consistent with the nucleo-cytoplasmic shuttling activity described above.

Example 10

The NES and NLS are Active in Both Primary and Transformed Cells

The simplest explanation for the differential localization of Apoptin in primary and transformed cells is that one of the localization signals is subject to cell type-specific regulation. For example, the NES might be active in primary and inactive in transformed cells. To test this model we analyzed localization of GFP-fused Apoptin fragments containing either the NLS or NES in primary and transformed cells.

GFP-Ap(42-88), which lacks both the NLS and NES, displayed a diffuse homogeneous localization pattern in both H1299 and PFF cells, similar to that of GFP alone. As expected, the GFP-Ap(1-48) and GFP-Ap(1-88) mutants, which contain the N-terminal NES but lack the C-terminal NLS, displayed a predominantly cytoplasmic localization pattern in PFFs. However, both mutants also localized to the cytoplasm in H1299 cells, indicating the NES is active in transformed cells. Conversely, the GFP-Ap(42-121) and GFP-Ap(82-121) mutants, which contain the C-terminal NLS but lack the N-terminal NES, localized to the nucleus in H1299 cells as well as in PFFs, indicating the NLS is active in primary cells. Thus, the NLS and NES are active in both primary and transformed cells. These results suggest that when uncoupled the NES and NLS function constitutively.

Example 11

Apoptin is a Multimer

Previous studies have shown that recombinant Apoptin aggregates in vitro (Leliveld et al., J. Biol. Chem., 278:9042-9051 (2003), raising the possibility that Apoptin functions as a multimer in vivo. To first test this possibility, whether cell type-specific localization could be restored in trans by co-expression of two Apoptin fragments, one containing the NLS and the other containing the NES, was investigated.

GFP-Ap-pmNLS, which lacks a functional NLS, localized to the cytoplasm of both H1299 cells and PFFs, whereas dsRed-Ap-pmNES, which lacks a functional NES, localized to the nucleus in both H1299 cells and PFFs. However, co-expression of GFP-Ap-pmNLS and dsRed-Ap-pmNES resulted in the localization of both proteins to the nucleus of H1299 cells and the cytoplasm of PFFs. These results suggest that Apoptin is a multimer in vivo and confirm that both localization signals are required for proper cell type-specific localization.

To confirm that Apoptin is a multimer in vivo and to map the multimerization domain a series of co-immunoprecipitation experiments was performed.

For multimerization experiments, ~$1 \times 10^7$ H1299 cells were transiently transfected with GFP-Apoptin truncation mutants using Effectene reagent. After 12 hours cells were infected with Ad-Apwt and incubated for a further 24 hours. Cells were then harvested by scraping, and lysed in Buffer X (50 mM Tris, pH 8.5, 250 mM NaCl, 1 mM EDTA, 1% NP40, Complete Mini tablet (Roche, Basel, Switzerland)) on ice for 20 min. Cell debris was removed by centrifugation and supernatants were incubated with 30 µl Ezview Red α-FLAG M2 affinity beads (Sigma) at 4° C. for 4 hours. Following incubation, beads were washed in Buffer X and bound proteins were eluted by boiling in SDS sample buffer at 95° C. for 5 min. Solubility analysis was conducted by infecting ~$1 \times 10^7$ H1299 or PFF cells with Ad-Apwt followed by incubation for 48 hours. Cells were then harvested by scraping, lysed in Buffer X, centrifuged and immunoprecipitated as described above. For APC1 association studies, $1 \times 10^7$ H1299 cells were transiently transfected with indicated FLAG-Apoptin constructs followed by 48 hr. incubation. Cells were then harvested and immunoprecipitated as indicated above.

Only derivatives containing the N-terminal third of Apoptin [GFP-Apwt, GFP-Ap(1-48), GFP-Ap(1-88), and Ap(1-48)-GFP-Ap(82-121)] co-immunoprecipitated with the FLAG-Apoptin, indicating that this region mediates protein multimerization.

To confirm the results of the co-immunoprecipitation experiments and to verify that multimerization is the basis for restoration of cell type-specific localization in trans, three additional Apoptin derivatives were analyzed in the trans-expression assay. Expression of dsRed-Apwt restored nuclear localization to the constitutively cytoplasmic GFP-Ap(1-88) mutant in transformed cells and maintained cytoplasmic localization in primary cells. By contrast, dsRed-Ap (82-121) failed to alter cytoplasmic localization of GFP-Ap (1-88) in transformed cells, indicating that the N-terminal multimerization domain is required for trans-association of the localization signals. These results show that the activity of a constitutively cytoplasmic mutant can be restored by expressing an NLS-containing C-terminal fragment in trans.

Example 12

The Apoptin NES is Critical for Proper Cell Type-Specific Localization

We next asked whether the specific sequence of Apoptin's NES and NLS were required for cell type-specific localization by determining whether they could be functionally substituted with heterologous localization signals.

Replacement of the Apoptin NLS with that of SV40 large T antigen (Ap-SV40NLS) resulted in nuclear localization in H1299 cells and predominantly cytoplasmic localization in PFFs. Thus, the SV40 large T antigen NLS can functionally substitute for the Apoptin NLS. By contrast, replacement of the Apoptin NES with that of Rev (Ap-RevNES) resulted in a similar localization pattern in both H1299 and PFFs, indicating that the specific sequence of the Apoptin NES is critical for proper cell type-specific localization.

Example 13

The Apoptin Multimerization Domain Overlaps with the NES and is Required for Cell Type-Specific Localization One explanation for the failure of the Rev NES to functionally substitute for the Apoptin NES is that the Apoptin NES provides an activity in addition to nuclear export. Because both the NES and multimerization domain map to the N-terminus, we reasoned that the NES might be an essential part of the multimerization domain. To test this possibility, the two NES derivatives, Ap-pmNES and Ap-RevNES, were analyzed for their ability to multimerize in the co-immunoprecipitation assay.

Compared to GFP-Apwt, the GFP-Ap-pmNES mutant showed a reduced ability to interact with FLAG-Apoptin. Significantly, GFP-Ap-RevNES, which contains a functional NES that differs at multiple residues from the Apoptin NES, failed to detectably co-immunoprecipitate with FLAG-Apoptin. Interestingly, the intermediate level of multimerization observed with the Ap-pmNES mutant was sufficient to confer function in the trans assay; however, close inspection revealed that Ap-pmNES was less effective than wild type Apoptin in mediating trans localization, which presumably reflected the decreased multimerization efficiency. Together, these results suggest that the Apoptin multimerization domain overlaps with the NES and is required for cell type-specific localization.

Example 14

The NLS Sequence Overlaps with the Domain Required for Association with APC1

The above experiments address the contribution of the NES and NLS to protein localization, but do not indicate if these sequences are required for the ability of Apoptin to induce apoptosis. To investigate the role of the NLS, a second NLS mutant in which lysine-116, arginine-117 and arginine-118 were mutated to alanine (Ap-pmNLS2) was constructed. This mutant protein retained partial nuclear localization in H1299 cells. We also analyzed the Ap-SV40NLS mutant, which localized exclusively in the nucleus in H1299 cells. To determine the ability of these two mutants to induce cell death in transformed cells, GFP-Apwt, GFP-Ap-pmNLS2 and GFP-Ap-SV40NLS were transiently expressed in H1299 cells and three days after transfection, cells were fixed, stained with DAPI and analyzed by microscopy for apoptotic morphology. As expected, cells expressing GFP-Apwt underwent pronounced apoptosis whereas the ability of the Ap-pmNLS2 and Ap-SV40NLS mutants to induce apoptosis was severely reduced.

To understand why the Ap-pmNLS2 and Ap-SV40NLS mutants failed to induce apoptosis in transformed cells even though they localized to the nucleus, we next monitored their ability to interact with the APC1 subunit of the APC/C, which interacts with the C-terminus of Apoptin as described herein. A triple FLAG-tagged version of each mutant was transiently transfected into H1299 cells and immunoprecipitated with an anti-FLAG antibody, and the immunoprecipitate analyzed for APC1 by immunoblotting. As expected, APC1 was present in the immunoprecipitate from wild type Apoptin, but not in that of the Ap-pmNLS2 or Ap-SV40NLS mutants despite the presence of both these mutants in the nucleus. These observations are consistent with the results described above and suggest that the NLS sequence overlaps with the domain required for association with APC1. Furthermore, these results indicate that nuclear localization in the absence of APC1 association is not sufficient to induce apoptosis.

To assess the involvement of the NES in Apoptin-induced cell death, we next investigated the ability of the Ap-pmNES mutant, which contains a wild type C-terminal domain and localizes to the nucleus in transformed and primary cells to interact with APC1 and induce apoptosis. Surprisingly, this mutant exhibited greatly reduced ability to interact with APC1 and failed to induce apoptosis in transformed and primary cells. The dnRan assay shows, as expected, that the Ap-pmNES mutant failed to undergo nucleo-cytoplasmic shuttling. Thus, the NES is required for optimal shuttling and apoptosis.

Example 15

Therapeutic Efficacy of Compounds that Modulate APC1

The therapeutic efficacy of compounds identified by a method described herein as inhibiting a function of APC/C are verified in an animal model.

A mouse model of human hepatic cancer is created by injecting s.c. in both flanks with $1 \times 10^7$ human hepatoma cells (HepG2; obtained from ATCC, Manassas, Va.) suspended in 200 µL of serum-free Hanks. The is administered a fragment of Apoptin including SEQ ID NO:16 or 17, an siRNA or antisense polynucleotide directed against APC1, or a control treatment such as a non-toxic, non-therapeutic peptide or polynucleotide. The animal model is then monitored for a change in its condition, e.g., as described in van der Eb et al., Cancer Gene Ther., 9:53-61 (2002).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying a candidate compound that modulates apoptosis, the method comprising:

contacting a sample comprising anaphase promoting complex subunit 1 (APC1) with a test compound, under conditions that allow the test compound to bind to APC1;

evaluating binding of the test compound to APC1, and identifying the test compound as a candidate compound that modulates apoptosis if the test compound binds to APC1.

2. The method of claim 1, further comprising evaluating an effect of the test compound on a function of APC1.

3. The method of claim 2, wherein the function of APC1 is ubiquitination of a target protein.

4. The method of claim 3, wherein the target protein is a cell cycle protein.

5. The method of claim 4, wherein the cell cycle protein is selected from the group consisting of Clb5, Cdc20, Cdh1, cyclin B1, Plk1, and securin.

6. The method of claim 1, wherein the sample comprises one or more components of anaphase promoting complex/cyclosome (APC/C).

7. The method of claim 6, wherein the sample comprises subunits 1-11 of the APC/C in a functional complex.

8. The method of claim 1, wherein the sample further comprises cdc20 activator protein.

9. The method of claim 1, further comprising evaluating the association of APC 1 with one or more subunits of APC/C.

10. The method of claim 1, wherein the test compound is an aptamer.

11. The method of claim 1, wherein the test compound comprises a polypeptide comprising at least 10 consecutive amino acids of Apoptin (SEQ ID NO:1).

12. The method of claim 11, wherein the polypeptide comprises SEQ ID NO:16 or 17.

13. The method of claim 1, wherein the test compound comprises a small molecule.

14. A method comprising:
contacting a sample comprising anaphase promoting complex subunit 1 (APC1) with a composition comprising a polypeptide comprising at least 10 consecutive amino acids of Apoptin (SEQ ID NO:1), under conditions that allow the test compound to bind to APC1; and
evaluating the binding of the composition to APC 1.

15. The method of claim 14, wherein the polypeptide comprises SEQ ID NO:16 or 17.

16. The method of claim 1, further comprising determining whether the test compound competes with a polypeptide comprising at least 10 consecutive amino acids of Apoptin (SEQ ID NO:1) for binding to APC1.

* * * * *

UNITED STATES PATENT AND TRADEMARK OFFICE
CERTIFICATE OF CORRECTION

| | | |
|---|---|---|
| PATENT NO. | : 7,566,548 B2 | Page 1 of 1 |
| APPLICATION NO. | : 11/204980 | |
| DATED | : July 28, 2009 | |
| INVENTOR(S) | : Michael Green | |

It is certified that error appears in the above-identified patent and that said Letters Patent is hereby corrected as shown below:

Column 46, line 60, claim 9 replace "APC 1" with --APC1--

Column 48, line 1, claim 14 replace "APC 1." with --APC1.--

Signed and Sealed this

Twenty-second Day of December, 2009

David J. Kappos
*Director of the United States Patent and Trademark Office*